US008147831B2

(12) United States Patent
Hansen et al.

(10) Patent No.: US 8,147,831 B2
(45) Date of Patent: *Apr. 3, 2012

(54) ANTI-CD19 ANTIBODIES

(75) Inventors: Hans J. Hansen, Picayune, MS (US);
Zhengxing Qu, Warren, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/907,262

(22) Filed: Oct. 19, 2010

(65) Prior Publication Data

US 2011/0052489 A1 Mar. 3, 2011

Related U.S. Application Data

(60) Division of application No. 12/266,999, filed on Nov. 7, 2008, now Pat. No. 7,902,338, which is a continuation-in-part of application No. 11/445,410, filed on Jun. 1, 2006, now Pat. No. 7,462,352, which is a division of application No. 10/903,858, filed on Aug. 2, 2004, now Pat. No. 7,109,304.

(60) Provisional application No. 60/491,282, filed on Jul. 31, 2003.

(51) Int. Cl.
*A61K 39/395* (2006.01)
*A61K 39/40* (2006.01)
*C07K 16/00* (2006.01)

(52) U.S. Cl. ............... 424/130.1; 424/133.1; 424/134.1; 424/136.1; 424/141.1; 424/143.1; 424/144.1; 424/152.1; 424/153.1; 424/155.1; 424/178.1

(58) Field of Classification Search .................. None
See application file for complete search history.

(56) References Cited

U.S. PATENT DOCUMENTS

| | | | |
|---|---|---|---|
| 5,530,101 A | 6/1996 | Queen et al. |
| 5,798,554 A | 8/1998 | Grimaldi et al. |
| 6,183,744 B1 | 2/2001 | Goldenberg et al. |
| 6,187,287 B1 | 2/2001 | Leung et al. |
| 6,306,393 B1 | 10/2001 | Goldenberg et al. |
| 6,653,104 B2 | 11/2003 | Goldenberg et al. |
| 7,109,304 B2 | 9/2006 | Hansen et al. |
| 7,462,352 B2 | 12/2008 | Hansen et al. |
| 2003/0133930 A1 | 7/2003 | Goldenberg et al. |
| 2008/0187966 A1 | 8/2008 | Simmons et al. |

FOREIGN PATENT DOCUMENTS

| | | |
|---|---|---|
| WO | 96/36360 | 11/1996 |
| WO | 00/74718 | 12/2000 |

OTHER PUBLICATIONS

MeSh Antigen CD80 Apr. 21, 2011, pp. 1-2.*
Levesque. Clincal & Experimental Immunology, 2009, 157:198-208.*
Tedder et al. 2009, Nat Rev Rheumatol 5:572-77.*
Awan et al. 2010, Blood 115:1204-13.*
Al-Katib et al. 2009, Clin Cancer Res 15:4038-45.*
Yazawa et al. 2005, Proc Natl Acad Sci USA 102:15178-83.*
Topp et al. 2011, J Clin Oncol 29:2493-98, Abstract only.*
Cardarelli et al. 2010, Cancer Immunol Immunother 59:257-65, Abstract only.*
Schwemmlein et al. 2007, Leukemia 21:1405-12, Abstract only.*
Bataille et al., "The phenotype of normal, reactive and malignant plasma cells. Identification of "many and multiple myelomas" and of new targets for myeloma therapy" Haematologica 91(9):1234-1240 (2006).
Cochlovius et al., "Treatment of Human B Cell Lymphoma Xenografts with a CD3 × CD19 Diabody and T Cells" the Journal of Immunology, 2000, 165:888-895.
Ek et al., "Treatment of Human B-Cell Precursor Leukemia in SCID Mice by Using a Combination of the anti-CD19 Immunotoxin B43-PAP with the Standard Chemotherapeutic Drugs Vincristine, Methylprednisolone, and L-Asparaginase", Leukemia and Lymphoma, vol. 31, pp. 143-149 (1998).
Ghetie et al., "Homodimers but not monomers of Rituxan (chimeric anti-CD20) induce apoptosis in human B-lymphoma cells and synergize with a chemotherapeutic agent and an immunotoxin", Blood 2001;97:1392-1398.
Ghetie et al., "Evaluation of Ricin A Chain-containing Immunotoxins Directed against CD19 and CD22 Antigens on Normal and Malignant Human B-Cells as Potential Reagents for in Vivo therapy", Cancer Research 48, 2610-2617, 1988.
Ghetie et al., "Homodimerization of tumor-reactive monoclonal antibodies markedly increases their ability to induce growth arrest or apoptosis of tumor cells", Proc. Natl. Acad. Sci. USA vol. 94, pp. 7509-7514 (1997).
Ghetie et al., "The Antitumor Activity of an Anti-CD22 Immunotoxin in SCID Mice with Disseminated Daudi Lymphoma is Enhanced by Either an anti-CD19 Antibody or an Anti-CD19 Immunotoxin", Blood, vol. 80, No. 9, pp. 2315-2320 (1992).
Hekman et al., "Initial experience with treatment of human B cell lymphoma with anti-CD19 monoclonal antibody", Cancer Immunol Immunother (1991) 32:364-372.
Ma et al., "Radioimmunotherapy for model B cell malignancies using 90Y-labeled anti-CD19 and anti-CD20 monoclonal antibodies", Leukemia (2002) 16, 60-66.
Matsushita et al., "Inhibitory Role of CD19 in the Progression of Experimental Autoimmune Encephalomyelitis by Regulating Cytokine Response", American Journal of Pathology vol. 168(3):812-821 (2006).

(Continued)

*Primary Examiner* — Chun Dahle
(74) *Attorney, Agent, or Firm* — Richard A. Nakashima

(57) ABSTRACT

The present invention provides humanized, chimeric and human anti-CD19 antibodies, anti-CD19 antibody fusion proteins, and fragments thereof that bind to a human B cell marker. Such antibodies, fusion proteins and fragments thereof are useful for the treatment and diagnosis of various B-cell disorders, including B-cell malignancies and autoimmune diseases. In more particular embodiments, the humanized anti-CD19 antibodies may comprise one or more framework region amino acid substitutions designed to improve protein stability, antibody binding and/or expression levels. In a particularly preferred embodiment, the substitutions comprise a Ser91Phe substitution in the hA19 VH sequence.

20 Claims, 9 Drawing Sheets

OTHER PUBLICATIONS

Mitchell et al., "Targeting Primary Human Ph+ B-Cell Precursor Leukemia-Engrafted SCID Mice Using Radiolabeled Anti-CD19 Monoclonal Antibodies", J Nucl Med 2003; 44:1105-1112.

Patti et al., "High-dose cyclophosphamide, etoposide and BCNU (CVB) with autologous stem cell rescue in malignant lymphomas", Eur. J. Haematol 1993: 51:18-24.

Pietersz et al., "In vitro and in vivo antitumour activity of a chimeric anti-CD19 antibody", Cancer Immunol Immunother (1995) 41:53-60.

Roguska et al., "A comparison of two murine monoclonal antibodies humanized by CDR-grafting and variable domain resurfacing", Protein Engineering vol. 9, No. 10, pp. 895-904, 1996.

Roguska et al., "Humanization of murine monoclonal antibodies through variable domain resurfacing", Proc. Natl. Acad. Sci. USA vol. 91, pp. 969-973, Feb. 1994.

Rowland et al., "Preclinical invesigation of the antitumour effects of anti-CD19-idarubicin immunoconjugates", Cancer Immunol Immunother (1993) 37:195-202.

Shan et al. "Signaling events involved in anti-CD20-induced apoptosis of malignant human B cells" Cancer Immunol Immunother (2000) 48:673-683.

Stone et al., "A phase I Study of Bolus Versus Continuous Infusion of the anti-CD19 Immunotoxin, IgG-HD37-dgA, in Patients with B-Cell Lymphoma", Blood, vol. 88, No. 4 Aug. 15, 1996, pp. 1188-1197.

Uckun et al., "Treatment of Therapy-Refractory B-Lineage Acute Lymphoblastic Leukemia with an Apoptosis-inducing CD19-directed Tyrosine Kinase Inhibitor", Clincial Cancer Research vol. 5, 3906-3913, Dec. 1999.

Uckun et al., "Detailed Studies on Expression and Function of CD19 Surface Determinant by Using B43 Monoclonal Antibody and the Clinical Potential of Anti-CD19 Immunotoxins", Blood, vol. 71(1):13-29 (1988).

Uckun et al., "Effective Immunochemotherapy of CALLA +Cu+ Human Pre-B Acute Lymphoblastic Leukemia in Mice with Severe Combined Immunodeficency Using B43 (anti-CD19) Pokeweed Antiviral Protein Immunotoxin Plus Cyclophosphamide", Blood, vol. 79(12):3116-3129 (1992).

Zola et al., "Preparation and characterization of a chimeric CD19 monoclonal antibody", Immunology and Cell Biology (1991) 69, 411-422.

* cited by examiner

```
GACATCCAGCTGACCCAGTCTCCAGCTTCTCTTTGGCTGTGTCTCTAGGGCAGAGGGCCACCATCTCCTGCAAGGCCAGCCAAAGTGTTGAT      90
  1                         10                        20            27 A B C
  D  I  Q  L  T  Q  S  P  A  S  L  A  V  S  L  G  Q  R  A  T  I  S  C  K  A  S  Q  S  V  D

TATGATGGTGATAGTTATTTGAACTGGTACCAACAGATTCCAGGACAGCCACCCAAACTCCTCATCTATGATGCATCCAATCTAGTTTCT     180
            30                        40                        50
  Y  D  G  D  S  Y  L  N  W  Y  Q  Q  I  P  G  Q  P  P  K  L  L  I  Y  D  A  S  N  L  V  S
  CDR1                                                                  CDR2

GGCATCCCACCCAGGTTTAGTGGCAGTGGGTCTGGGACAGACTTCACCCTCAACATCCATCCTGTGGAGAAGTGGATGCTGCAACCTAT     270
                    60                        70                        80
  G  I  P  P  R  F  S  G  S  G  S  G  T  D  F  T  L  N  I  H  P  V  E  K  V  D  A  A  T  Y

CACTGTCAGCAAAGTACTGAAGATCCGTGGACGTTCGGTGGAGGGACCAAGCTGGAGATCAAACGT                            336
              90                       100                 108
  H  C  Q  Q  S  T  E  D  P  W  T  F  G  G  G  T  K  L  E  I  K  R
        CDR3
```

FIG. 1A

```
CAGGTCCAACTGCAGGAGTCTGGGGCTGAGCTGGTGAGGCCTGGGTCCTCAGTGAAGATTTCCTGCAAGGCTTCTGGTTATGCATTCAGT        90
  1                                    10                           20                      30
  Q  V  Q  L  Q  E  S  G  A  E  L  V  R  P  G  S  S  V  K  I  S  C  K  A  S  G  Y  A  F  S

AGCTACTGGATGAACTGGGTGAAGCAGAGGCCTGGACAGGGTCTTGAGTGGATTGGACAGATTTGGCCTGGAGATGGTGATACTAACTAC       180
                          40                      50   52 A                                60
  S  Y  W  M  N  W  V  K  Q  R  P  G  Q  G  L  E  W  I  G  Q  I  W  P  G  D  G  D  T  N  Y
      CDR1                                                 CDR2

AATGGAAAGTTCAAGGGTAAAGCCACTCTGACTGCCGACGAATCCTCCAGCACAGCCTACATGCAACTCAGCAGCCTACGGATCTGAGGAC      270
              60                      70                      80  82 A B C
  N  G  K  F  K  G  K  A  T  L  T  A  D  E  S  S  S  T  A  Y  M  Q  L  S  S  L  R  S  E  D

TCTGCGGTCTATTCTTGTGCAAGACGGGAGACTACGACGGTTATTACTATGCTATGGACTACTGGGGCCAAGGGACCACGGTC              336
              90                      100 A B C D E F G
  S  A  V  Y  S  C  A  R  R  E  T  T  T  V  G  R  Y  Y  Y  A  M  D  Y  W  G  Q  G  T  T  V
                                CDR3

ACCGTCTCCTCA                                                                                     336
110       113
  T  V  S  S
```

FIG. 1B

```
           1                        10                        20                          27 A B C D   30
REIVk      DIQMTQSPSSLSASVGDRVTITC QASQ----DIKYLN WY
cA19Vk     ...L....A..AV.L.Q.A..S. K...SVDY.GDS.. ..
hA19Vk     ...L..................... K...SVDY.GDS.. ..

40                     50                              60                        70
REIVk      QQTPGKAPKLLIY EANSLQA GVPSRFSGSGSGTDYTFTIS
cA19Vk     ...I..QP..... D.SN.VS ..I.P........F.LN.H.
hA19Vk     ...I......... D.SN.VS ..I.P................

80                        90                        100
REIVk      SLQPEDIATYYC QQYQSLPYT FGQGTKLQITR
cA19Vk     PVEKV.A....  H...STED.W ..G......K.
hA19Vk     .............H...STED.W ..G......K.
```

FIG. 3A

```
         1                   10                  20                   30          40
EUVH     QVQLVQSGAEVKKPGSSVKVSCKASGGTFS SYWLH WVRQA
cA19VH   ···QE···LVR······I··········· ·YA·· ·MN·K·R
hA19VH   ···Q·························· ·YA·· ·MN···R 50 52A           60               70
EUVH     PGQGLEWMG GIVPMFGPPNYAQKFQG RATITADESTNTAY
cA19VH   ········· ·I·Q·W·GD·DT··NG·K·K ·L······
hA19VH   ········· ·I·Q·W·GD·DT··NG···K ················SS 80 82ABC                90            100 ABCDEFG
EUVH     MELSSLRSEDTAFYFCAG GYGIYS------PE
cA19VH   ·Q···············S·V·S·· RETTTVGRYYYAMDY
hA19VH   ··················S····· RETTTVGRYYYAMDY 103          110
NEWMVH   WGQGSLVTVSS
cA19VH   ····TT·····
hA19VH   ····TT·····
```

FIG. 3B

```
GACATCCAGCTGACCCAGTCTCCATCATCTCTGAGCGCATCTGTTGGAGATAGGGTCACTATCACTTGTAAGGCCAGCAAAGTGTTGAT     90
  1                    10                    20                27 A B C
  D  I  Q  L  T  Q  S  P  S  S  L  S  A  S  V  G  D  R  V  T  I  T  C  K  A  S  Q  S  V  D

TATGATGGTGATAGTTATTTGAACTGGTACCAGCAGATTCCAGGGAAAGCACCTAAAATTGTTGATCTACGATGCTTCGAATCTAGTTTCT    180
  D                    30                    40                    50
  Y  D  G  D  S  Y  L  N  W  Y  Q  Q  I  P  G  K  A  P  K  L  L  I  Y  D  A  S  N  L  V  S
           CDR1                                                       CDR2

GGTATCCCTCCTCGATTCTCTGGCAGCGGATCTGGGACAGATTACACTTTCACCATCAGCTCTCTTCAACCAGAAGACATTGCAACATAT    270
                        60                    70                    80
  G  I  P  P  R  F  S  G  S  G  S  G  T  D  Y  T  F  T  I  S  S  L  Q  P  E  D  I  A  T  Y

CACTGTCAGCAAAGTACTGAAGATCCGTGGACGTTCGGTGGAGGCACCAAGCTACAGATCAAACGT                            336
                        90                   100              108
  H  C  Q  Q  S  T  E  D  P  W  T  F  G  G  G  T  K  L  Q  I  K  R
           CDR3
```

FIG. 4A

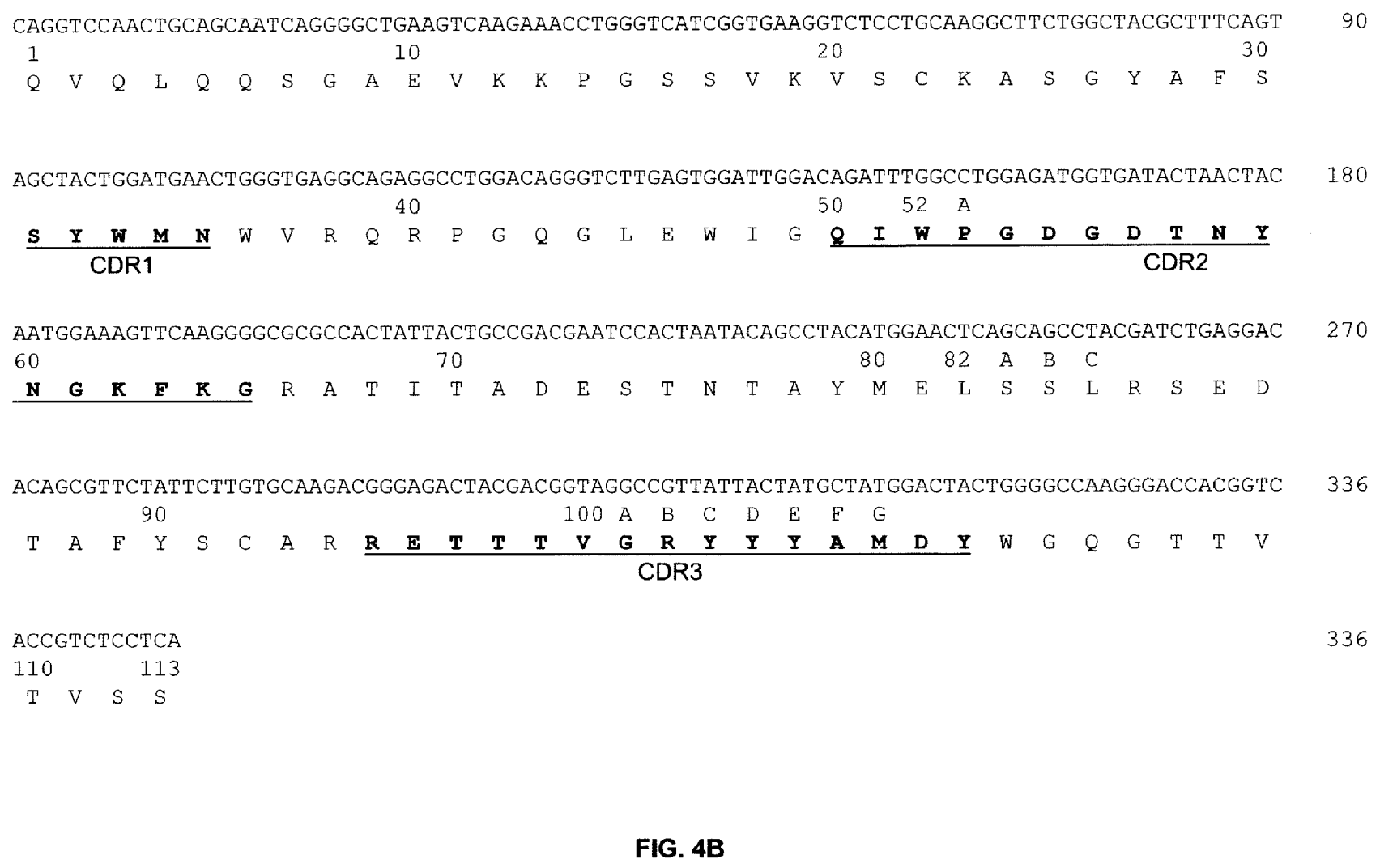

```
                                                                              90
CAGGTCCAACTGCAGCAATCAGGGGCTGAAGTCAAGAAACCTGGGGTCATCGGTGAAGGTCTCCTGCAAGGCTTCTCTGGCTACGCTTTCAGT
 1                  10                  20                       30
 Q  V  Q  L  Q  Q  S  G  A  E  V  K  K  P  G  S  S  V  K  V  S  C  K  A  S  G  Y  A  F  S

180
AGCTACTGGATGAACTGGGTGAGGCAGAGGCCAGGACAGGGTCTTGAGTGGATTGGACAGATTTGGCCTGGAGATGGTGATACTAACTAC
         40                  50          52 A                              CDR2
 S  Y  W  M  N  W  V  R  Q  R  P  G  Q  G  L  E  W  I  G  Q  I  W  P  G  D  G  D  T  N  Y
    CDR1

270
AATGGAAAGTTCAAGGGGCGCGCCACTATTACTGCCGACGAATCCACTAATACAGCCTACATGGAACTCAGCAGCCTACGATCTGAGGAC
     60                       70                  80     82 A B C
 N  G  K  F  K  G  R  A  T  I  T  A  D  E  S  T  N  T  A  Y  M  E  L  S  S  L  R  S  E  D

336
ACAGCGGTTCTATTCTTGTGCAAGACGGGAGACTACGGAGACTACGGAGACTACTGGGGCCAAGGACCACGGTC
                 90                   100 A B C D E F G
 T  A  F  Y  S  C  A  R  R  E  T  T  T  V  G  R  Y  Y  Y  A  M  D  Y  W  G  Q  G  T  T  V
                           CDR3

336
ACCGTCTCCTCA
110        113
 T  V  S  S
```

FIG. 4B

SEQUENCE LISTING

```
<160> NUMBER OF SEQ ID NOS: 31

<210> SEQ ID NO 1
<211> LENGTH: 336
<212> TYPE: DNA
<213> ORGANISM: Artificial Sequence
<220> FEATURE:
<223> OTHER INFORMATION: Description of Artificial Sequence: Synthetic
      anti-CD19 antibody, cA19
<220> FEATURE:
<221> NAME/KEY: CDS
<222> LOCATION: (1)..(336)

<400> SEQUENCE: 1 gac atc cag ctg acc cag tct cca gct tct ttg gct gtg tct cta ggg      48
Asp Ile Gln Leu Thr Gln Ser Pro Ala Ser Leu Ala Val Ser Leu Gly
  1               5                  10                  15 cag agg gcc acc atc tcc tgc aag gcc agc caa agt gtt gat tat gat      96
Gln Arg Ala Thr Ile Ser Cys Lys Ala Ser Gln Ser Val Asp Tyr Asp
             20                  25                  30 ggt gat agt tat ttg aac tgg tac caa cag att cca gga cag cca ccc     144
```

```
Gly Asp Ser Tyr Leu Asn Trp Tyr Gln Gln Ile Pro Gly Gln Pro Pro
            35                  40                  45 aaa ctc ctc atc tat gat gca tcc aat cta gtt tct ggc atc cca ccc      192
Lys Leu Leu Ile Tyr Asp Ala Ser Asn Leu Val Ser Gly Ile Pro Pro
        50                  55                  60 agg ttt agt ggc agt ggg tct ggg aca gac ttc acc ctc aac atc cat      240
Arg Phe Ser Gly Ser Gly Ser Gly Thr Asp Phe Thr Leu Asn Ile His
 65                  70                  75                  80 cct gtg gag aag gtg gat gct gca acc tat cac tgt cag caa agt act      288
Pro Val Glu Lys Val Asp Ala Ala Thr Tyr His Cys Gln Gln Ser Thr
                85                  90                  95 gaa gat ccg tgg acg ttc ggt gga ggg acc aag ctg gag atc aaa cgt      336
Glu Asp Pro Trp Thr Phe Gly Gly Gly Thr Lys Leu Glu Ile Lys Arg
            100                 105                 110

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      anti-CD19 antibody, cA19

<400> SEQUENCE: 2

Asp Ile Gln Leu Thr Gln Ser Pro Ala Ser Leu Ala Val Ser Leu Gly
  1               5                  10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

<210> SEQ ID NO 3
<211> LENGTH: 372
<212> TYPE: DNA
<213> ORGANISM: Artificial Sequence
<220> FEATURE:
<223> OTHER INFORMATION: Description of Artificial Sequence: Synthetic
      anti-CD19 antibody, cA19
<220> FEATURE:
<221> NAME/KEY: CDS
<222> LOCATION: (1)..(372)

<400> SEQUENCE: 3 cag gtc caa ctg cag gag tct ggg gct gag ctg gtg agg cct ggg tcc       48
Gln Val Gln Leu Gln Glu Ser Gly Ala Glu Leu Val Arg Pro Gly Ser
  1               5                  10                  15 tca gtg aag att tcc tgc aag gct tct ggt tat gca ttc agt agc tac       96
Ser Val Lys Ile Ser Cys Lys Ala Ser Gly Tyr Ala Phe Ser Ser Tyr
                20                  25                  30 tgg atg aac tgg gtg aag cag agg cct gga cag ggt ctt gag tgg att      144
Trp Met Asn Trp Val Lys Gln Arg Pro Gly Gln Gly Leu Glu Trp Ile
            35                  40                  45 gga cag att tgg cct gga gat ggt gat act aac tac aat gga aag ttc      192
Gly Gln Ile Trp Pro Gly Asp Gly Asp Thr Asn Tyr Asn Gly Lys Phe
        50                  55                  60
```

```
aag ggt aaa gcc act ctg act gcc gac gaa tcc tcc agc aca gcc tac    240
Lys Gly Lys Ala Thr Leu Thr Ala Asp Glu Ser Ser Thr Ala Tyr
 65                  70                  75                  80 atg caa ctc agc agc cta cga tct gag gac tct gcg gtc tat tct tgt    288
Met Gln Leu Ser Ser Leu Arg Ser Glu Asp Ser Ala Val Tyr Ser Cys
             85                  90                  95 gca aga cgg gag act acg acg gta ggc cgt tat tac tat gct atg gac    336
Ala Arg Arg Glu Thr Thr Thr Val Gly Arg Tyr Tyr Tyr Ala Met Asp
100                 105                 110 tac tgg ggc caa ggg acc acg gtc acc gtc tcc tca                    372
Tyr Trp Gly Gln Gly Thr Thr Val Thr Val Ser Ser
            115                 120
```

<210> SEQ ID NO 4
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-CD19 antibody, cA19

<400> SEQUENCE: 4

```
Gln Val Gln Leu Gln Glu Ser Gly Ala Glu Leu Val Arg Pro Gly Ser
  1               5                  10                  15

Ser Val Lys Ile Ser Cys Lys Ala Ser Gly Tyr Ala Phe Ser Ser Tyr
             20                  25                  30

Trp Met Asn Trp Val Lys Gln Arg Pro Gly Gln Gly Leu Glu Trp Ile
         35                  40                  45

Gly Gln Ile Trp Pro Gly Asp Gly Asp Thr Asn Tyr Asn Gly Lys Phe
     50                  55                  60

Lys Gly Lys Ala Thr Leu Thr Ala Asp Glu Ser Ser Thr Ala Tyr
 65                  70                  75                  80

Met Gln Leu Ser Ser Leu Arg Ser Glu Asp Ser Ala Val Tyr Ser Cys
             85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
            115                 120
```

<210> SEQ ID NO 5
<211> LENGTH: 108
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ile Lys Tyr
             20                  25                  30

Leu Asn Trp Tyr Gln Gln Thr Pro Gly Lys Ala Pro Lys Leu Leu Ile
         35                  40                  45

Tyr Glu Ala Asn Ser Leu Gln Ala Gly Val Pro Ser Arg Phe Ser Gly
     50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Tyr Gln Ser Leu Pro Tyr
             85                  90                  95

Thr Phe Gly Gln Gly Thr Lys Leu Gln Ile Thr Arg
            100                 105
```

```
<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Chimeric
      cA19Vk antibody

<400> SEQUENCE: 6

Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
             20                  25                  30

Gly Asp Ser Tyr Leu Asn Trp Tyr Gln Gln Ile Pro Gly Gln Pro Pro
         35                  40                  45

Lys Leu Leu Ile Tyr Asp Ala Ser Asn Leu Val Ser Gly Ile Pro Pro
     50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Gln Ile Lys Arg
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized hA19Vk antibody

<400> SEQUENCE: 7

Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
             20                  25                  30

Gly Asp Ser Tyr Leu Asn Trp Tyr Gln Gln Ile Pro Gly Lys Ala Pro
         35                  40                  45

Lys Leu Leu Ile Tyr Asp Ala Ser Asn Leu Val Ser Gly Ile Pro Pro
     50                  55                  60

Arg Phe Ser Gly Ser Gly Ser Gly Thr Asp Tyr Thr Phe Thr Ile Ser
 65                  70                  75                  80

Ser Leu Gln Pro Glu Asp Ile Ala Thr Tyr His Cys Gln Gln Ser Thr
                 85                  90                  95

Glu Asp Pro Trp Thr Phe Gly Gly Gly Thr Lys Leu Gln Ile Lys Arg
            100                 105                 110

<210> SEQ ID NO 8
<211> LENGTH: 117
<212> TYPE: PRT
<213> ORGANISM: Homo sapiens

<400> SEQUENCE: 8

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Trp Leu His Trp Val Arg Gln Ala Pro Gly Gln Gly Leu Glu Trp Met
```

```
                    35                  40                  45
Gly Gly Ile Val Pro Met Phe Gly Pro Pro Asn Tyr Ala Gln Lys Phe
            50                  55                  60

Gln Gly Arg Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu Trp Gly Gly Gly Ser Leu
            100                 105                 110

Val Thr Val Ser Ser
        115

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Chimeric
      cA19VH antibody

<400> SEQUENCE: 9

Gln Val Gln Leu Gln Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Arg Ser Glu Asp Ser Ala Val Tyr Ser Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence: Synthetic
      humanized hA19VH antibody

<400> SEQUENCE: 10

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Ala Phe Ser Ser Tyr
                20                  25                  30

Trp Met Asn Trp Val Arg Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Arg Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Ser Cys
                85                  90                  95
```

```
Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 11
<211> LENGTH: 11
<212> TYPE: PRT
<213> ORGANISM: Homo sapiens

<400> SEQUENCE: 11

Trp Gly Gln Gly Ser Leu Val Thr Val Ser Ser
  1               5                  10

<210> SEQ ID NO 12
<211> LENGTH: 336
<212> TYPE: DNA
<213> ORGANISM: Artificial Sequence
<220> FEATURE:
<223> OTHER INFORMATION: Description of Artificial Sequence: Synthetic
      humanized anti-CD19 antibody, hA19Vk
<220> FEATURE:
<221> NAME/KEY: CDS
<222> LOCATION: (1)..(336)

<400> SEQUENCE: 12 gac atc cag ctg acc cag tct cca tca tct ctg agc gca tct gtt gga      48
Asp Ile Gln Leu Thr Gln Ser Pro Ser Ser Leu Ser Ala Ser Val Gly
  1               5                  10                  15 gat agg gtc act atc act tgt aag gcc agc caa agt gtt gat tat gat      96
Asp Arg Val Thr Ile Thr Cys Lys Ala Ser Gln Ser Val Asp Tyr Asp
             20                  25                  30 ggt gat agt tat ttg aac tgg tac cag cag att cca ggg aaa gca cct     144
Gly Asp Ser Tyr Leu Asn Trp Tyr Gln Gln Ile Pro Gly Lys Ala Pro
         35                  40                  45 aaa ttg ttg atc tac gat gct tcg aat cta gtt tct ggt atc cct cct     192
Lys Leu Leu Ile Tyr Asp Ala Ser Asn Leu Val Ser Gly Ile Pro Pro
     50                  55                  60 cga ttc tct ggc agc gga tct ggg aca gat tac act ttc acc atc agc     240
Arg Phe Ser Gly Ser Gly Ser Gly Thr Asp Tyr Thr Phe Thr Ile Ser
 65                  70                  75                  80 tct ctt caa cca gaa gac att gca aca tat cac tgt cag caa agt act     288
Ser Leu Gln Pro Glu Asp Ile Ala Thr Tyr His Cys Gln Gln Ser Thr
                 85                  90                  95 gaa gat ccg tgg acg ttc ggt gga ggg acc aag cta cag atc aaa cgt     336
Glu Asp Pro Trp Thr Phe Gly Gly Gly Thr Lys Leu Gln Ile Lys Arg
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized anti-CD19 antibody, hA19Vk

<400> SEQUENCE: 13

Asp Ile Gln Leu Thr Gln Ser Pro Ser Ser Leu Ser Ala Ser Val Gly
  1               5                  10                  15

Asp Arg Val Thr Ile Thr Cys Lys Ala Ser Gln Ser Val Asp Tyr Asp
             20                  25                  30

Gly Asp Ser Tyr Leu Asn Trp Tyr Gln Gln Ile Pro Gly Lys Ala Pro
         35                  40                  45
```

```
Lys Leu Leu Ile Tyr Asp Ala Ser Asn Leu Val Ser Gly Ile Pro Pro
 50                  55                  60

Arg Phe Ser Gly Ser Gly Ser Gly Thr Asp Tyr Thr Phe Thr Ile Ser
 65                  70                  75                  80

Ser Leu Gln Pro Glu Asp Ile Ala Thr Tyr His Cys Gln Gln Ser Thr
                 85                  90                  95

Glu Asp Pro Trp Thr Phe Gly Gly Gly Thr Lys Leu Gln Ile Lys Arg
            100                 105                 110

<210> SEQ ID NO 14
<211> LENGTH: 372
<212> TYPE: DNA
<213> ORGANISM: Artificial Sequence
<220> FEATURE:
<223> OTHER INFORMATION: Description of Artificial Sequence: Synthetic
      humanized anti-CD19 antibody, hA19VH
<220> FEATURE:
<221> NAME/KEY: CDS
<222> LOCATION: (1)..(372)

<400> SEQUENCE: 14 cag gtc caa ctg cag caa tca ggg gct gaa gtc aag aaa cct ggg tca     48
Gln Val Gln Leu Gln Gln Ser Gly Ala Glu Val Lys Lys Pro Gly Ser
 1               5                  10                  15 tcg gtg aag gtc tcc tgc aag gct tct ggc tac gct ttc agt agc tac     96
Ser Val Lys Val Ser Cys Lys Ala Ser Gly Tyr Ala Phe Ser Ser Tyr
                20                  25                  30 tgg atg aac tgg gtg agg cag agg cct gga cag ggt ctt gag tgg att    144
Trp Met Asn Trp Val Arg Gln Arg Pro Gly Gln Gly Leu Glu Trp Ile
            35                  40                  45 gga cag att tgg cct gga gat ggt gat act aac tac aat gga aag ttc    192
Gly Gln Ile Trp Pro Gly Asp Gly Asp Thr Asn Tyr Asn Gly Lys Phe
     50                  55                  60 aag ggg cgc gcc act att act gcc gac gaa tcc act aat aca gcc tac    240
Lys Gly Arg Ala Thr Ile Thr Ala Asp Glu Ser Thr Asn Thr Ala Tyr
 65                  70                  75                  80 atg gaa ctc agc agc cta cga tct gag gac aca gcg ttc tat tct tgt    288
Met Glu Leu Ser Ser Leu Arg Ser Glu Asp Thr Ala Phe Tyr Ser Cys
                 85                  90                  95 gca aga cgg gag act acg acg gta ggc cgt tat tac tat gct atg gac    336
Ala Arg Arg Glu Thr Thr Thr Val Gly Arg Tyr Tyr Tyr Ala Met Asp
            100                 105                 110 tac tgg ggc caa ggg acc acg gtc acc gtc tcc tca                    372
Tyr Trp Gly Gln Gly Thr Thr Val Thr Val Ser Ser
        115                 120

<210> SEQ ID NO 15
<211> LENGTH: 124
<212> TYPE: PRT
<213> ORGANISM: Artificial Sequence
<220> FEATURE:
<223> OTHER INFORMATION: Description of Artificial Sequence: Synthetic
      humanized anti-CD19 antibody, hA19VH

<400> SEQUENCE: 15

Gln Val Gln Leu Gln Gln Ser Gly Ala Glu Val Lys Lys Pro Gly Ser
 1               5                  10                  15

Ser Val Lys Val Ser Cys Lys Ala Ser Gly Tyr Ala Phe Ser Ser Tyr
                20                  25                  30

Trp Met Asn Trp Val Arg Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
     50                  55                  60
```

```
Lys Gly Arg Ala Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Ser Cys
                 85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Lys Ala Ser Gln Ser Val Asp Tyr Asp Gly Asp Ser Tyr Leu Asn
 1               5                  10                  15
```

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Asp Ala Ser Asn Leu Val Ser
 1               5
```

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Gln Gln Ser Thr Glu Asp Pro Trp Thr
 1               5
```

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Ser Tyr Trp Met Asn
 1               5
```

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Gln Ile Trp Pro Gly Asp Gly Asp Thr Asn Tyr Asn Gly Lys Phe Lys
 1               5                  10                  15
Gly

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Glu Thr Thr Thr Val Gly Arg Tyr Tyr Tyr Ala Met Asp Tyr
 1               5                  10                  15

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 22

Gly Gly Gly Ser
 1

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 23

Gly Gly Gly Gly Ser Gly Gly Gly Gly Ser Gly Gly Gly Gly Ser
 1               5                  10                  15

<210> SEQ ID NO 24
<211> LENGTH: 126
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atcacttgta aggccagcca agtgttgat tatgatggtg atagttattt gaactggtac        60
cagcagattc cagggaaagc acctaaattg ttgatctacg atgcttcgaa tctagttttct    120 ggtatc                                                                126

<210> SEQ ID NO 25
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgctgacagt gatatgttgc aatgtcttct ggttgaagag agctgatggt gaaagtgtaa      60
tctgtcccag atccgctgcc agagaatcga ggagggatac cagaaactag attcgaagca    120
tcgta                                                                 125
```

<210> SEQ ID NO 26
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tccgacatcc agctgaccca gtctccatca tctctgagcg catctgttgg agatagggtc      60
actatcactt gtaaggccag ccaaag                                          86

<210> SEQ ID NO 27
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctccttgag atctgtagct tggtccctcc accgaacgtc cacggatctt cagtactttg      60
ctgacagtga tatgttgcaa t                                               81

<210> SEQ ID NO 28
<211> LENGTH: 137
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctggctacgc tttcagtagc tactggatga actgggtgag gcagaggcct ggacagggtc      60
ttgagtggat tggacagatt tggcctggag atggtgatac taactacaat ggaaagttca     120
aggggcgcgc cactatt                                                    137

<210> SEQ ID NO 29
<211> LENGTH: 129
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgtagtctcc cgtcttgcac aagaatagaa cgctgtgtcc tcagatcgta ggctgctgag      60
ttccatgtag gctgtattag tggattcgtc ggcagtaata gtggcgcgcc ccttgaactt     120
tccattgta                                                             129

<210> SEQ ID NO 30
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caggtccaac tgcagcaatc aggggctgaa gtcaagaaac ctgggtcatc ggtgaaggtc      60
tcctgcaagg cttctggcta cgctttcagt agc                                  93

```
<210> SEQ ID NO 31
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaggagacg gtgaccgtgg tcccttggcc ccagtagtcc atagcatagt aataacggcc    60
taccgtcgta gtctcccgtc ttgcacaag                                      89
```

ANTI-CD19 ANTIBODIES

RELATED APPLICATIONS

This application is a divisional of U.S. patent application Ser. No. 12/266,999, (now issued U.S. Pat. No. 7,902,338) filed Nov. 7, 2008, which was a continuation-in-part of U.S. patent application Ser. No. 11/445,410 (now issued U.S. Pat. No. 7,462,352), filed Jun. 1, 2006, which was a divisional of U.S. patent application Ser. No. 10/903,858 (now issued U.S. Pat. No. 7,109,304), filed Aug. 2, 2004, which claimed priority to a provisional U.S. Patent Application No. 60/491,282, filed Jul. 31, 2003, the contents of each of which are incorporated herein by reference in their entirety.

BACKGROUND OF THE INVENTION

1. Field of the Invention

The present invention relates to anti-CD19 antibodies, particularly humanized, chimeric and human anti-CD19 antibodies, particularly monoclonal antibodies (MAbs) and fragments thereof, either naked or conjugated to at least one therapeutic and/or diagnostic agent, and methods of use thereof. In particular, the anti-CD19 antibodies can be used for treating B cell disease such as, for example, a malignancy, an inflammatory disease or disorder, or an autoimmune disease. In more particular embodiments, the anti-CD19 antibodies may comprise one or more substituted amino acids designed to optimize a physical and/or physiological characteristic of the antibody.

2. Description of Related Art

The immune system of vertebrates consists of a number of organs and cell types which have evolved to accurately recognize foreign antigens, specifically bind to, and eliminate/destroy such foreign antigens. Lymphocytes, among other cell types, are critical to the immune system. Lymphocytes are divided into two major sub-populations, T cells and B cells. Although inter-dependent, T cells are largely responsible for cell-mediated immunity and B cells are largely responsible for antibody production (humoral immunity).

In humans, each B cell can produce an enormous number of antibody molecules. Such antibody production typically ceases (or substantially decreases) when a foreign antigen has been neutralized. Occasionally, however, proliferation of a particular B cell will continue unabated and may result in a cancer known as a B cell lymphoma or leukemia. B-cell lymphomas, such as the B-cell subtype of non-Hodgkin's lymphoma, are significant contributors to cancer mortality.

The response of B-cell malignancies to various forms of treatment is mixed. For example, in cases in which adequate clinical staging of non-Hodgkin's lymphoma is possible, field radiation therapy can provide satisfactory treatment. Still, about one-half of the patients die from the disease. Devesa et al., J. Nat'l Cancer Inst. 79:701 (1987).

The majority of chronic lymphocytic leukemias are of the B-cell lineage. Freedman, Hematol. Oncol. Clin. North Am. 4:405 (1990). This type of B-cell malignancy is the most common leukemia in the Western world. Goodman et al., Leukemia and Lymphoma 22: 1 (1996). The natural history of chronic lymphocytic leukemia falls into several phases. In the early phase, chronic lymphocytic leukemia is an indolent disease, characterized by the accumulation of small mature functionally-incompetent malignant B-cells having a lengthened life span. Eventually, the doubling time of the malignant B-cells decreases and patients become increasingly symptomatic. While treatment can provide symptomatic relief, the overall survival of the patients is only minimally affected. The late stages of chronic lymphocytic leukemia are characterized by significant anemia and/or thrombocytopenia. At this point, the median survival is less than two years. Foon et al., Annals Int. Medicine 113:525 (1990). Due to the very low rate of cellular proliferation, chronic lymphocytic leukemia is resistant to cytotoxic drug treatment. Traditional methods of treating B-cell malignancies, including chemotherapy and radiotherapy, have limited utility due to toxic side effects.

B cells comprise cell surface proteins which can be utilized as markers for differentiation and identification. One such human B-cell marker is a CD19 antigen and is found on mature B cells but not on plasma cells. CD19 is expressed during early pre-B cell development and remains until plasma cell differentiation. CD19 is expressed on both normal B cells and malignant B cells whose abnormal growth can lead to B-cell lymphomas. For example, CD19 is expressed on B-cell lineage malignancies, including, but not limited to non-Hodgkin's lymphoma, chronic lymphocytic leukemia, and acute lymphoblastic leukemia.

A potential problem with using non-human monoclonal antibodies (e.g., murine monoclonal antibodies) is typically lack of human effector functionality. In other words, such antibodies may be unable to mediate complement-dependent lysis or lyse human target cells through antibody-dependent cellular toxicity or Fc-receptor mediated phagocytosis. Furthermore, non-human monoclonal antibodies can be recognized by the human host as a foreign protein and, therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response.

The use of chimeric antibodies is more preferred because they do not elicit as strong a HAMA response as murine antibodies Chimeric antibodies are antibodies which comprise portions from two or more different species. For example, Liu, A. Y. et al, "Production of a Mouse-Human Chimeric Monoclonal Antibody to CD20 with Potent Fc-Dependent Biologic Activity" J. Immun. 139/10:3521-3526 (1987), describe a mouse/human chimeric antibody directed against the CD20 antigen. See also, PCT Publication No. WO 88/04936. However, no information is provided as to the ability, efficacy or practicality of using such chimeric antibodies for the treatment of B cell disorders in the reference. It is noted that in vitro functional assays (e.g., complement-dependent lysis (CDC); antibody dependent cellular cytotoxicity (ADCC), etc.) cannot inherently predict the in vivo capability of a chimeric antibody to destroy or deplete target cells expressing the specific antigen. See, for example, Robinson, R. D. et al., "Chimeric mouse-human anti-carcinoma antibodies that mediate different anti-tumor cell biological activities," Hum. Antibod. Hybridomas 2:84-93 (1991) (chimeric mouse-human antibody having undetectable ADCC activity). Therefore, the potential therapeutic efficacy of a chimeric antibody can only truly be assessed by in vivo experimentation, preferably in the species of interest for the specific therapy.

One approach that has improved the ability of murine monoclonal antibodies to be effective in the treatment of B-cell disorders has been to conjugate a radioactive label or chemotherapeutic agent to the antibody, such that the label or agent is localized at the tumor site. For example, studies indicate that $^{90}Y$ labeled anti-CD19 antibodies can be used to reduce lymphoma in mice (McDevitt et al., Leukemia 16:60, 2002), anti-CD19 antibodies conjugated to idarubicin result in tumor regression in an experimental model (Rowland et al., Cancer Immunol. Immunother., 37:195, 1993), and $^{125}I$ and ¹¹¹In radiolabeled anti-CD19 is specifically taken up in tumor bearing organs (Mitchell et al., J. Nucl. Med., 44: 1105, 2003). Combination therapy with an anti-CD19 antibody is also disclosed in Ek et al., Leuk. Lymphoma 31: 143 (1998) and Uckun et al., Blood, 79:3116 (1992). Treatment of human B cell lymphoma with an anti-CD19 antibody and anti-CD3 × anti-CD19 diabody is disclosed in Hekman et al., Cancer Immunol. Immunother., 32:364 (1991) and Cochlovius et al., J. Immunol., 165:888 (2000), respectively.

However, these approaches have not eliminated the obstacles associated with using murine antibodies, despite the fact that many patients with lymphoma who have received prior aggressive cytotoxic chemotherapy are immune suppressed, thus having lower HAMA rates than lymphoma patients who have not been heavily pretreated.

Inflammatory diseases, including autoimmune diseases are also a class of diseases associated with B-cell disorders. The most common treatments are corticosteroids and cytotoxic drugs, which can be very toxic. These drugs also suppress the entire immune system, can result in serious infection, and have adverse affects on the bone marrow, liver and kidneys. Other therapeutics that have been used to treat Class III autoimmune diseases have been directed against T-cells and macrophages. There is a need for more effective methods of treating autoimmune diseases, particularly Class III autoimmune diseases.

SUMMARY OF THE INVENTION

The present invention provides humanized, chimeric and human anti-CD19 monoclonal antibodies and fragments thereof, and antibody fusion proteins and fragments thereof for the treatment of B cell lymphomas and leukemias and autoimmune disorders in humans and other mammals. The antibodies, fusion proteins and fragments thereof can be used alone, conjugated to at least one diagnostic and/or therapeutic agent or in combination with other treatment modalities.

Methods of use of the claimed antibodies may include treatment of mammalian subjects, such as humans or domestic animals, with one or more humanized, chimeric or human anti-CD19 antibodies, alone, as an antibody fusion protein, as a therapeutic conjugate alone or as part of an antibody fusion protein, in combination, or as a multimodal therapy, with other antibodies, other therapeutic agents or immunomodulators or as an immunoconjugate linked to at least one therapeutic agent, therapeutic radionuclide or immunomodulator. These humanized, chimeric and human anti-CD19 antibodies can also be used as a diagnostic imaging agent alone, in combination with other diagnostic imaging agents, and/or in conjunction with therapeutic applications. Disease states that may be treated include neoplasias, preferably B cell related lymphomas and leukemias, such as non-Hodgkin's lymphoma, chronic lymphocytic leukemia, acute lymphoblastic leukemia, or multiple myeloma. Other disease states that may be treated include autoimmune diseases, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, and fibrosing alveolitis. The skilled artisan will realized that these are not limiting and any disease state in which CD19 expressing cells play a role may potentially be treated with the claimed anti-CD19 antibodies, alone or in combination.

Various embodiments concern antibody fusion proteins and fragments thereof comprising at least two anti-CD19 MAbs or fragments thereof, or at least one anti-CD19 MAb or fragment thereof and at least one second MAb or fragment thereof, other than the anti-CD19 MAb or fragment thereof. Second antibodies of use may include antibodies against other B cell associated or B cell specific antigens, such as CD20, CD22, CD23, CD80 or HLA-DR. The multispecific and/or fusion proteins can be either naked or conjugated to at least one therapeutic and/or diagnostic agent.

The humanized, chimeric and human anti-CD19 MAbs and fragments thereof, and antibody fusion proteins and fragments thereof may be administered alone, either naked or conjugated to a therapeutic or diagnostic agent, or in combination with another naked antibody, fragment or immunoconjugate. Also, naked or conjugated anti-CD19 antibodies and fragments thereof, and antibody fusion proteins and fragments thereof may be administered in combination with at least one therapeutic agent or diagnostic agent that is not conjugated to an, anti-CD19 antibody or fragment thereof, or fusion protein or fragment thereof.

Other embodiments relate to DNA sequences encoding a humanized, chimeric or human anti-CD19 antibody and fragment thereof, and antibody fusion protein and fragment thereof. Likewise, a vector and host cell containing the DNA sequence is also contemplated. The claimed methods also include methods of making the humanized, chimeric and human anti-CD19 antibodies and fragments thereof, and fusion proteins and fragments thereof.

Particular embodiments relate to anti-CD19 MAbs or fragments thereof that contain specific murine CDRs that have specificity for CD19. These MAbs can be humanized, chimeric or human anti-CD19 MAbs. In preferred embodiments, the antibodies may comprise one or more substituted amino acid residues, such as the substitution of a corresponding murine framework region amino acid residue in a human framework region sequence of a humanized antibody. Preferred framework region amino acids that are candidates for substitution include those that are located close or adjacent to one or more CDR amino acid side chains, or that otherwise affect the stability and/or expression levels of the encoded protein. In a most preferred embodiment, the substitution includes replacement of a serine residue with a phenylalanine residue at Kabat residue 91 of the VH sequence of a humanized A19 (hA19) antibody.

BRIEF DESCRIPTION OF THE FIGURES

FIG. 1 discloses the Vk, the variable light chain, and the VH, the variable heavy chain, sequences of cA19, a chimeric anti-CD19 antibody. The CDR region sequences are shown in bold and underlined. The nucleotides are numbered sequentially. Kabat's Ig molecule numbering is used for amino acid residues as shown by the numbering above the amino acid residues. The amino acid residues numbered by letters are the insertion residues defined by Kabat numbering scheme. The insertion residues have the same preceding digits as that of the previous residue. For example, residues 82, 82A, 82B, and 82C in FIG. 1B are indicated as 82, A, B, and C, respectively. The light chain variable region is shown in FIG. 1A (SEQ ID NO:1 and SEQ ID NO:2) and the heavy chain variable region is shown in FIG. 1B (SEQ ID NO:3 and SEQ ID NO:4).

FIG. 3 compares the amino acid sequences of the variable light chain (Vk) and variable heavy chain (VH) of human antibodies, the chimeric and the humanized anti-CD19 antibodies. FIG. 3A compares the amino acid sequences of the variable light chain (Vk) of the human antibody, (REIVk, SEQ ID NO:5), a chimeric antibody, (cA19Vk, SEQ ID NO:6), and a humanized antibody, (hA19Vk, SEQ ID NO:7), and FIG. 3B compares the amino acid sequences of the variable heavy chain (VH) of the human antibodies, EU (SEQ ID NO:8) and NEWM (FR4 only, SEQ ID NO:11), the chimeric antibody, (cA19VH, SEQ ID NO:9) and a humanized antibody (hA19VH, SEQ ID NO:10).

FIG. 4 discloses the amino acid sequences of the humanized anti-CD19 antibody, hA19, light chain V gene, (hA19Vk) (FIG. 4A, SEQ ID NO:12 and SEQ ID NO:13), and heavy chain V gene, hA19VH (FIG. 4B, SEQ ID NO:14 and SEQ ID NO:15). The nucleotide sequences are shown in lowercase. Numbering of Vk and VH amino acid residues is the same as that in FIG. 1.

FIG. 5A shows both unconjugated hA19 (closed triangles) and cA19 (closed circles) blocked the binding of $^{125}$I-hA19 to Raji cells. FIG. 5B shows hA19 (closed circles) and c19 (closed squares) competed equally well for the binding of $^{125}$I-cA19 to Raji cells. Increasing concentrations of either cA19 or hA19 blocked the binding of radiolabeled hA19 or cA19 to Raji cells respectively.

DETAILED DESCRIPTION OF THE INVENTION

Definitions

Figure 2:
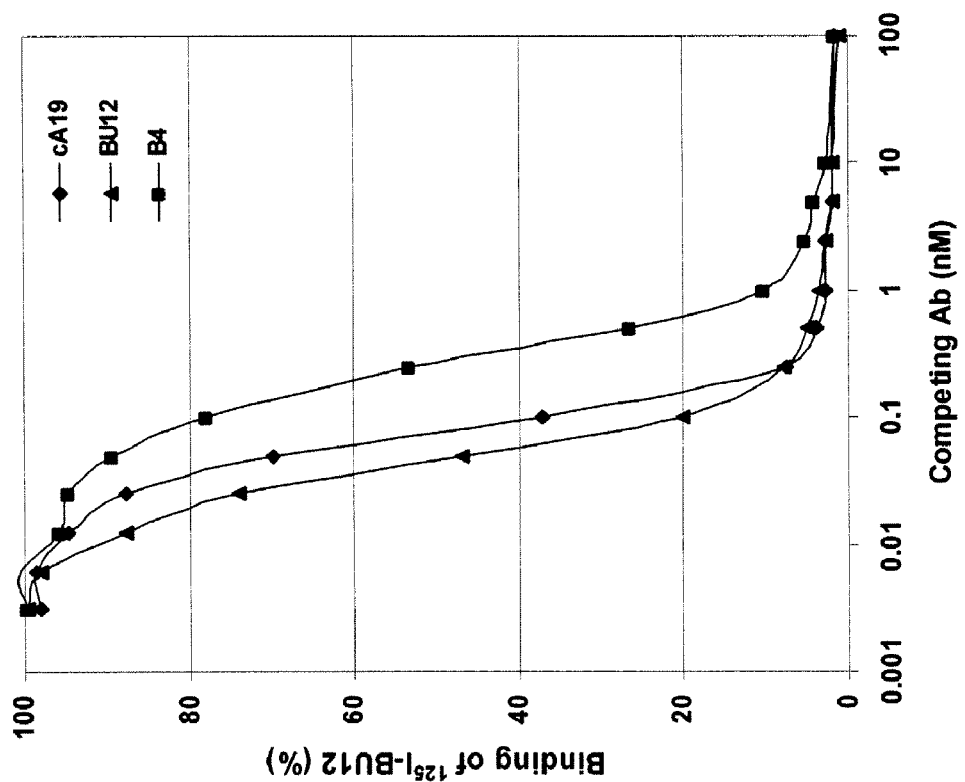
FIG. 2 shows the results of cell surface competitive binding assay to compare the binding specificity of the cA19 antibody with that of other anti-CD19 antibodies, BU12 and B4. Increasing concentrations of cA19 blocked the binding of radiolabeled BU12 to Raji cells in a similar fashion as the unlabeled BU12 and B4, indicating these antibodies recognize similar or overlap epitopes of the CD19 molecule.

Unless otherwise specified, "a" or "an" as used herein means "one or more."

Unless otherwise specified, terms are used in accordance with their plain and ordinary meaning.

An "antibody," as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An "antibody fragment" is a portion of an antibody such as F(ab)$_2$, F(ab')$_2$, Fab, Fab', Fv, sFv and the like. Regardless of structure, an antibody fragment binds with the same antigen that is recognized by the intact antibody. For example, an anti-CD19 monoclonal antibody fragment binds with an epitope of CD19. Antibody fragments include isolated fragments consisting of the variable regions, such as "Fv" fragments consisting of the variable regions of the heavy and light chains or recombinant single chain polypeptide molecules in which light and heavy variable regions are connected by a peptide linker ("scFv proteins").

A "naked antibody" is generally an entire antibody which is not conjugated to a therapeutic agent. This is so because the Fc portion of the antibody molecule provides effector functions, such as complement fixation and ADCC (antibody dependent cell cytotoxicity), which set mechanisms into action that may result in cell lysis. However, it is possible that the Fc portion is not required for therapeutic function, with other mechanisms, such as apoptosis, coming into play. "Naked antibodies" include both polyclonal and monoclonal antibodies, as well as certain recombinant antibodies, such as chimeric, humanized or human antibodies.

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody.

A "human antibody" is an antibody that contains human variable and constant region sequences. For example, human antibodies may be obtained from transgenic mice that have been engineered to produce human antibodies in response to antigenic challenge. In this technique, elements of the human heavy and light chain loci are introduced into strains of mice derived from embryonic stem cell lines that contain targeted disruptions of the murine endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, which are incorporated in their entirety by reference.

A "therapeutic agent" is a molecule or atom which is administered separately, concurrently or sequentially with an antibody moiety or conjugated to an antibody moiety, i.e., antibody or antibody fragment, or a sub fragment, and is useful in the treatment of a disease. Examples of therapeutic agents include antibodies, antibody fragments, drugs, toxins, enzymes, oligonucleotides, antisense and RNAi oligonucleotides, nucleases, hormones, immunomodulators, chelators, boron compounds, photoactive agents or dyes and radioisotopes.

A "diagnostic agent" is a molecule or atom which may be administered conjugated to an antibody moiety, i.e., antibody or antibody fragment, or subfragment, and is useful in diagnosing a disease by locating the cells containing a target antigen. Useful diagnostic agents include, but are not limited to, radioisotopes, dyes, contrast agents, ultrasound-enhancing agents, optical-enhancing agents, fluorescent compounds or molecules and enhancing agents (e.g. paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, ultrasound, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), DOTA, NOTA, porphyrins, polyamines, crown ethers, bis-thiosemicarbazones, polyoximes, and like groups known to be useful for this purpose. Chelates are coupled to the peptides or proteins using standard chemistries. The chelate is normally linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radio-imaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macro cyclic polyethers, which are of interest for stably binding nuclides, such as $^{223}$Ra for RAIT are encompassed.

An "immunoconjugate" is a conjugate of an antibody component with a therapeutic or diagnostic agent.

An "expression vector" is a nucleic acid molecule, preferably a double-stranded DNA molecule, comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A "recombinant host cell" may be any prokaryotic or eukaryotic cell that contains either a cloning vector or expression vector. This term also includes those prokaryotic or eukaryotic cells, as well as a transgenic animal, that have been genetically engineered to contain the cloned gene(s) in the chromosome or genome of the host cell or cells of the host animal. Suitable mammalian host cells include myeloma cells, such as SP2/0 cells, and NS0 cells, as well as Chinese Hamster Ovary (CH0) cells, hybridoma cell lines and other mammalian host cells useful for expressing antibodies. Also useful to express MAbs and other fusion proteins, is a human cell line, PER.C6 disclosed in WO 0063403 A2. Most preferred host cells are cells that have been engineered to contain a Bcl-EEE gene or other apoptosis inhibitor, that have been pre-adapted to grow and be transfected in serum-free or low-serum media. Examples of such host cells are disclosed in U.S. patent application Ser. Nos. 11/187,863, filed Jul. 25, 2005 and 11/487,215, filed Jul. 14, 2006, the text of each of which is incorporated herein by reference in its entirety. Special transgenic animals with a modified immune system are particularly useful for making fully human antibodies.

As used herein, the term "antibody fusion protein" refers to a recombinantly produced antigen-binding molecule comprising one or more of the same or different single-chain antibody or antibody fragment segments with the same or different specificities. Antibody fusion proteins may comprise an antibody or fragment thereof attached to another protein or peptide, such as a therapeutic agent, toxin, cytokine, hormone or other protein or peptide. In other embodiments, antibody fusion proteins may comprise at least a first and second antibody or antibody fragment. Where fusion proteins comprise two or more antibodies or fragments, the valency of the fusion protein indicates how many binding arms or sites the fusion protein has to a single antigen or epitope; i.e., monovalent, bivalent, trivalent or multivalent. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope.

A multispecific antibody is an antibody that can bind simultaneously to at least two targets that are of different structure, e.g., two different antigens, two different epitopes on the same antigen, or a hapten and/or an antigen or epitope. One specificity would be for a B-cell, T-cell, myeloid-, plasma-, and mast-cell antigen or epitope. Another specificity could be to a different antigen on the same cell type, such as CD20, CD19, CD20, CD21, CD23, CD46, CD80, HLA-DR, CD74, and CD22 on B-cells. Multispecific, multivalent antibodies are constructs that have more than one binding site, and the binding sites are of different specificity. For example, a diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific fusion proteins can be produced using molecular engineering.

Domestic animals include large animals such as horses, cattle, sheep, goats, llamas, alpacas, and pigs, as well as companion animals. In a preferred embodiment, the domestic animal is a horse. Companion animals include animals kept as pets. These are primarily dogs and cats, although small rodents, such as guinea pigs, hamsters, rats, and ferrets, are also included, as are subhuman primates such as monkeys. In a preferred embodiment the companion animal is a dog or a cat.

Overview

As discussed above, anti-CD19 antibodies that are unconjugated or labeled with a therapeutic radionuclide, have failed to provide high rates of objective and lasting responses in patients with intermediate or aggressive forms of B-cell lymphoma. The present invention provides humanized, chimeric or human anti-CD19 antibodies and antibody fusion proteins useful for treatment of mammalian subjects, humans and domestic animals, alone, as a conjugate or administered in combination with other therapeutic agents, including other naked antibodies and antibody therapeutic conjugates.

The anti-CD19 MAbs preferably contain specific murine CDRs from one or more murine or chimeric anti-CD19 MAbs that have specificity for the CD19 antigen. The anti-CD19 MAbs are humanized, chimeric or human MAbs. The CDRs of the light chain variable region of the anti-CD19 MAb preferably comprises CDR1 comprising amino acids KASQSVDYDGDSYLN (SEQ ID NO:16); CDR2 comprising amino acids DASNLVS (SEQ ID NO:17); and CDR3 comprising amino acids QQSTEDPWT (SEQ ID NO:18); and the heavy chain variable region CDR1 comprising amino acids SYWMN (SEQ ID NO:19); CDR2 comprising amino acids QIWPGDGDTNYNGKFKG (SEQ ID NO:20) and CDR3 comprising amino acids RETTTVGRYYYAMDY (SEQ ID NO:21).

In a preferred embodiment, the humanized anti-CD19 MAb or fragment thereof comprises the CDRs of a murine anti-CD19 MAb and the framework (FR) regions of the light and heavy chain variable regions of a human antibody and the light and heavy chain constant regions of a human antibody, while retaining substantially the B-cell, and B-cell lymphoma and leukemia cell targeting of the parent murine anti-CD19 MAb, and wherein the CDRs of the light chain variable region of the anti-CD19 MAb comprise CDR1 comprising amino acids KASQSVDYDGDSYLN (SEQ ID NO:16); CDR2 comprising amino acids DASNLVS (SEQ ID NO:17); and CDR3 comprising amino acids QQSTEDPWT (SEQ ID NO:18); and the CDRs of the heavy chain variable region of the anti-CD19 MAb comprise CDR1 comprising amino acids SYWMN (SEQ ID NO:19); CDR2 comprising amino acids QIWPGDGDTNYNGKFKG (SEQ ID NO:20) and CDR3 comprising amino acids RETTTVGRYYYAMDY (SEQ ID NO:21). The humanized anti-CD19 MAb or fragment thereof may further contain in the FRs of the light and heavy chain variable regions of the antibody at least one amino acid from the corresponding FRs of the murine MAb. Specifically, the humanized anti-CD19 MAb or fragment thereof may contain at least one amino acid residue selected from residues 5, 27, 28, 40, 48, 91, 94, 107 and 108 of the murine heavy chain variable region of FIG. 4A and at least one amino acid residue selected from residues 4, 39, 58, 60, 87, 100, and 107 of the murine light chain variable region FIG. 4B. In a more preferred embodiment, the humanized A19 antibody (hA19) contains each of the substituted murine FR amino acid residues listed above. One or more of the murine amino acid sequences can be maintained in the human FR regions of the light and heavy variable chains if necessary to maintain proper binding or to enhance binding to the CD19 antigen. More preferably the humanized anti-CD19 MAb or fragment thereof comprises the hA19Vk (SEQ ID NO:7) of FIG. 3A and the hA19VH (SEQ ID NO:10) of FIG. 3B. Most preferably, the humanized anti-CD19 MAb comprises an additional FR substitution of a serine residue with a phenylalanine residue at Kabat residue 91 of the hA19VH (SEQ ID NO:10) sequence.

The preferred chimeric anti-CD19 (cA19) MAb or fragment thereof comprises the CDRs of a murine anti-CD19 MAb and the FR regions of the light and heavy chain variable regions of the murine anti-CD19 MAb, i.e., the Fvs of the parental murine MAb, and the light and heavy chain constant regions of a human antibody, wherein the chimeric anti-CD19 MAb or fragment thereof retains substantially the B-cell, and B-cell lymphoma and leukemia cell targeting of the murine anti-CD19 MAb, wherein the CDRs of the light chain variable region of the anti-CD19 MAb comprises CDR1 comprising amino acids KASQSVDYDGDSYLN (SEQ ID NO:16); CDR2 comprising amino acids DASNLVS (SEQ ID NO:17); and CDR3 comprising amino acids QQSTEDPWT (SEQ ID NO:18); and the CDRs of the heavy chain variable region of the anti-CD19 MAb comprises CDR1 comprising amino acids SYWMN (SEQ ID NO:19); CDR2 comprising amino acids QIWPGDGDTNYNGKFKG and CDR3 comprising amino acids RETTTVGRYYYAMDY (SEQ ID NO:21). More preferably the chimeric anti-CD19 MAb or fragment thereof comprises the light and heavy chain variable region sequences of the chimeric anti-CD19 MAb shown in FIGS. 1A and 1B, respectively, designated cA19Vk (SEQ ID NO:6) and cA19VH (SEQ ID NO:9).

Various embodiments also encompass a human anti-CD19 MAb or fragment thereof comprising the light and heavy chain variable and constant regions of a human antibody, wherein said human anti-CD19 MAb retains substantially the B-cell, and B-cell lymphoma and leukemia cell targeting and cell binding characteristics of a murine anti-CD19 MAb, wherein the CDRs of the light chain variable region of the human anti-CD19 MAb comprises the same CDRs (SEQ ID NOs:16-21) as set forth above for the chimeric and humanized anti-CD19 MAbs and as shown in FIGS. 1A and 1B, and 3A and 3B, respectively.

Certain embodiments are also intended to encompass antibody fusion proteins or fragments thereof comprising at least two anti-CD19 MAbs or fragments thereof, as described above. The antibody fusion protein or fragment thereof is also intended to encompass an antibody fusion protein or fragment thereof comprising at least one first anti-CD19 MAb or fragment thereof as described above and at least one second MAb or fragment thereof, other than the anti-CD19 MAb or fragment described above. More preferably this second MAb is a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PlGF, ED-B fibronectin, an oncogene, an oncogene product, CD66a-d, necrosis antigens, Ii, IL-2, T101, TAC, IL-6, TRAIL-R1 (DR4) and TRAIL-R2 (DR5) or a combination thereof, and even an anti-CD19 MAb that is directed to a different epitope than the anti-CD19 MAb described herein. The antibody fusion proteins may be composed of one anti-CD19 MAb and one or more of the second MAbs to provide specificity to different antigens, and are described in more detail below.

The humanized, chimeric and human anti-CD19 antibody may possess enhanced affinity binding with the epitope, as well as antitumor and anti-B-cell activity, as a result of amino acid mutation and manipulation of the sequences in the variable region to obtain a superior therapeutic agent for the treatment of B-cell disorders, including B-cell lymphomas and leukemias and autoimmune diseases. Modification to the binding specificity, affinity or avidity of an antibody is known and described in WO 98/44001, as affinity maturation, and this application summarizes methods of modification and is incorporated in its entirety by reference.

It may also be desirable to modify the antibodies to improve effector function, e.g., so as to enhance antigen-dependent cell-mediated cytotoxicity (ADCC) and/or complement dependent cytotoxicity (CDC) of the antagonist. One or more amino acid substitutions or the introduction of cysteine in the Fc region may be made, thereby improving internalization capability and/or increased complement-mediated cell killing and ADCC. See Caron et al., J. Ex. Med. 176:1191-1195 (1991) and Shopes, Brit. J. Immunol. 148: 2918-2022 (1992), incorporated herein by reference in their entirety. An antibody fusion protein may be prepared that has dual Fc regions with both enhanced complement lysis and ADCC capabilities.

Certain embodiments are also directed to DNA sequences comprising a nucleic acid encoding a MAb or fragment thereof selected from the group consisting of: (a) an anti-CD19 MAb or fragment thereof as described herein, (b) an antibody fusion protein or fragment thereof comprising at least two of the anti-CD19 MAbs or fragments thereof, (c) an antibody fusion protein or fragment thereof comprising at least one first MAb or fragment thereof comprising the anti-CD19 MAb or fragment thereof as described herein and at least one second MAb or fragment thereof, other than the antiCD19 MAb or fragment thereof, and (d) an antibody fusion protein or fragment thereof comprising at least one first MAb or fragment thereof comprising the anti-CD19 MAb or fragment thereof and at least one second MAb or fragment thereof, wherein the second MAb is a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, 1a, HM1.24, HLA-DR, tenescin, ED-B fibronectin, IL-6, VEGF, PlGF, TRAIL-R1 (DR4) and TRAIL-R2 (DR5) or a combination thereof.

Also encompassed are expression vectors comprising the DNA sequences. These vectors contain the light and heavy chain constant regions and the hinge region of the human immunoglobulin, in the case of vectors for use in preparing the humanized, chimeric and human anti-CD19 MAbs or antibody fusion proteins thereof or fragments thereof. These vectors additionally contain, where required, promoters that express the MAbs in the selected host cell, immunoglobulin enhancers and signal or leader sequences. Vectors that are particularly useful in the present invention are pdHL2 or GS, particularly when used to express a chimeric, humanized or human antibody, such as IgGs, where the vector codes for the heavy and light chain constant regions and hinge region of IgG1. More preferably, the light and heavy chain constant regions and hinge region are from a human ED myeloma immunoglobulin, where optionally at least one of the amino acids in the allotype positions is changed to that found in a different IgG1 allotype, and wherein optionally amino acid 253 of the heavy chain of EU based on the EU number system may be replaced with alanine. See Edelman et al., Proc. Natl. Acad. Sci USA 63: 78-85 (1969), incorporated herein in its entirety by reference.

Host cells containing the DNA sequences encoding the anti-CD19 MAbs or fragments thereof or antibody fusion proteins or fragments thereof or host cells containing the vectors that contain these DNA sequences are encompassed by the present invention. Particularly useful host cells are mammalian cells, more specifically lymphocytic cells, such as myeloma cells, discussed in more detail below.

Also encompassed are methods of expressing the anti-CD19 MAb or fragment thereof or antibody fusion protein or fragment thereof comprising: (a) transfecting a mammalian cell with a DNA sequence encoding the anti-CD19 MAbs or fragments thereof or antibody fusion proteins or fragments thereof, and (b) culturing the cell transfected with the DNA sequence that secretes the anti-CD19 or fragment thereof or antibody fusion protein or fragment thereof. Known techniques may be used that include a selectable marker on the vector so that host cells that express the MAbs and the marker can be easily selected.

The present invention particularly encompasses B-lymphoma cell, leukemia cell and/or autoimmune cell targeting diagnostic or therapeutic conjugates comprising an antibody component comprising an anti-CD19 MAb or fragment thereof or an antibody fusion protein or fragment thereof that binds to the target cell that is conjugated or otherwise attached to at least one diagnostic or at least one therapeutic agent.

The diagnostic conjugate comprises an antibody component comprising an anti-CD19 MAb or fragment thereof or an antibody fusion protein or fragment thereof, wherein the diagnostic agent comprises at least one photoactive diagnostic agent, more preferably wherein the label is a radioactive label with an energy between 60 and 4,000 keV or a non-radioactive label. The radioactive label is preferably a gamma-, beta- or positron-emitting isotope and is selected from the group consisting of $^{125}$I, $^{131}$I, $^{123}$I, $^{124}$I, $^{86}$Y, $^{186}$Re, $^{62}$Cu, $^{64}$Cu, $^{111}$In, $^{67}$Ga, $^{68}$Ga, $^{99m}$Tc, $^{94m}$Tc, $^{18}$F, $^{11}$C, $^{13}$N, $^{15}$O, $^{76}$Br and combinations thereof.

The diagnostic conjugate may utilize a diagnostic agent, such as a contrast agent, for example, such as manganese, iron or gadolinium, or including an ultrasound-enhancing agent. In one embodiment, the ultrasound-enhancing agent is a liposome that comprises a chimerized or humanized anti-CD19 antibody or fragment thereof. Also preferred, the ultrasound enhancing agent is a liposome that is gas filled. Similarly, a bispecific antibody can be conjugated to a contrast agent. For example, the bispecific antibody may comprise more than one image enhancing agent for use in ultrasound imaging. The ultrasound enhancing agent can be a liposome, and preferably, the liposome comprises a bivalent DTP A peptide covalently attached to the outside surface of the liposome. Also preferred, the liposome is gas filled.

The therapeutic conjugate comprises an antibody component, such as an antibody fusion protein or fragment thereof, wherein each of said MAbs or fragments thereof are bound to at least one therapeutic agent. The therapeutic conjugate preferably is selected from the group consisting of a radioactive label, an immunomodulator, a hormone, an enzyme, an oligonucleotide, a photoactive therapeutic agent, a cytotoxic agent, which may be a drug or a toxin, and a combination thereof. Useful drugs include those drugs that possess a pharmaceutical property selected from the group consisting of antimitotic, alkylating, antimetabolite, antibiotic, alkaloid, antiangiogenic, apoptotic agents and combinations thereof, as well as antisense oligonucleotides and RNA molecules, such as short double stranded RNA molecules that activate the RNA interference pathway. More specifically, the drugs may be selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, thalidomide and its derivatives, antagonists, endostatin, taxols, camptothecins, anthracyclines, taxanes, and their analogs, and a combination thereof. The toxins may be selected from the group consisting of ricin, abrin, alpha toxin, saporin, onconase, i.e., ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

Other therapeutic agents suitable for use include anti-angiogenic agents (or angiogenesis inhibitors). These agents are suitable for use in combination therapy or for conjugating antibodies to, for example, angiostatin, endostatin, vasculostatin, canstatin and maspin, as well as the use of antibodies against angiogenesis factors, such as vascular endothelium growth factor (VEGF), placental growth factor (P1GF), ED-B fibronectin, and against other vascular growth factors. Single and double stranded oligonucleotides are a new class of therapeutic agents, and include, for example, antisense oligonucleotides, such as antisense bcl-2, and molecules, such as double stranded RNA molecules, that activate the RNA interference pathway and cause highly specific inhibition of gene expression, such as inhibition of bcl-2. Inhibition of bcl-2 (and related bcl family molecules) in a cell inhibits the anti-apoptotic activity of bcl-2 and promotes apoptosis of the cell. See Zangemeister-Wittke, Ann N Y Acad. Sci. 1002: 90-4 (2003).

Useful therapeutic conjugates are immunomodulators selected from the group consisting of a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins, such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons -alpha, -beta or -gamma, and stem cell growth factor, such as "S1 factor". More specifically, immunomodulators, such as IL-1, IL-2, IL-3, IL-6, IL-10, IL-12, IL-18, IL-21, interferon, TNF-alpha or -beta or a combination thereof may be of use.

Particularly useful therapeutic conjugates include one or more radioactive labels that have an energy between 60 and 700 keV. Such radioactive labels may be selected from the group consisting of $^{225}$Ac, $^{67}$Ga, $^{90}$Y, $^{111}$In, $^{131}$I, $^{125}$I, $^{186}$Re, $^{188}$Re, $^{177}$Lu, $^{32}$P, $^{64}$Cu, $^{212}$Bi, $^{213}$Bi, $^{211}$At and combinations thereof. Other useful therapeutic conjugates are photoactive therapeutic agents, such as a chromogen or dye.

The claimed methods encompass methods of treating a B-cell disease in a subject, such as a mammal, including humans, domestic or companion pets, such as dogs and cats. B cell diseases that can be treated by the methods include any disease which involves unwanted or undesirable B cell growth or activity, and includes malignancies such as lymphoma or leukemia or an autoimmune disease. The methods involve administering to the subject a therapeutically effective amount of an anti-CD19 MAb or a fragment thereof, formulated in a pharmaceutically acceptable vehicle. This therapy may utilize a "naked antibody" that does not have a therapeutic agent bound to it. The administration of the "naked anti-CD19 antibody" can be supplemented by administering to the subject concurrently or sequentially a therapeutically effective amount of another therapeutic agent, such as a second "naked antibody" that binds to or is reactive with another antigen on the surface of the target cell or that has other functions, such as effector functions in the Fc portion of the MAb, that is therapeutic and which is discussed herein. Preferred additional MAbs are at least one humanized, chimeric, human or murine (in the case of non-human animals) MAb selected from the group consisting of a MAb reactive with CD4, CD5, CD8, CD14, CD15, CD19, CD20, CD21, CD22, CD23, CD25, CD30, CD33, CD37, CD38, CD40, CD40L, CD45, CD46, CD52, CD54, CD74, CD80, CD126, CD138, B7, HM1.24, HLA-DR, an angiogenesis factor, tenascin, VEGF, PIGF, ED-B fibronectin, an oncogene, an oncogene product, CD66a-d, necrosis antigens, Ii, IL-2, MUC-1, T01, TAC, IL-6, TRAIL-R1 (DR4) and TRAIL-R2 (DR5) formulated in a pharmaceutically acceptable vehicle. In other embodiments, the anti-CD19 antibody may be conjugated to one or more therapeutic or diagnostic agents.

Both the naked anti-CD19 therapy alone or in combination with other naked MAbs as discussed above can be further supplemented with the administration, either concurrently or sequentially, of a therapeutically effective amount of at least one therapeutic agent, formulated in a pharmaceutically acceptable vehicle. As discussed herein the therapeutic agent may comprise a cytotoxic agent, a radioactive label, an immunomodulator, a hormone, an oligonucleotide (such as an antisense or RNAi oligonucleotide), an enzyme, a photoactive therapeutic agent or a combination thereof, formulated in a pharmaceutically acceptable vehicle.

In another therapeutic method, both the naked anti-CD19 therapy alone or in combination with other naked MAbs, as discussed above, can be further supplemented with the administration, either concurrently or sequentially, of a therapeutically effective amount of at least one therapeutic conjugate, described herein and formulated in a pharmaceutically acceptable vehicle. The antibody component of the therapeutic conjugate comprises at least one humanized, chimeric, human or murine (for non-human subjects) MAb selected from the group consisting of a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, HM1.24, HLA-DR, an angiogenesis factor, tenascin, VEGF, PIGF, ED-B fibronectin, an oncogene, an oncogene product, CD66a-d, necrosis antigens, Ii, IL-2, T101, TAC, IL-6, MUC-1, TRAIL-R1 (DR4) and TRAIL-R2 (DR5), formulated in a pharmaceutically acceptable vehicle. As discussed herein the therapeutic agent may comprise a cytotoxic agent, a radioactive label, an immunomodulator, a hormone, a photoactive therapeutic agent or a combination thereof, formulated in a pharmaceutically acceptable vehicle.

Other embodiments concern methods of treating a B-cell lymphoma or leukemia or an autoimmune disease in a subject comprising administering to a subject a therapeutically effective amount of an antibody fusion protein or fragment thereof comprising at least two anti-CD19 MAbs or fragments thereof or comprising at least one anti-CD19 MAb or fragment thereof and at least one additional MAb, preferably selected from the group consisting of MAbs reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, HM1.24, HLA-DR, tenascin, VEGF, PIGF, ED-B fibronectin, MUC-1, an oncogene, an oncogene product, CD66a-d, necrosis antigens, Ii, IL-2, T101, TAC, IL-6, TRAIL-R1 (DR4) and TRAIL-R2 (DR5) formulated in a pharmaceutically acceptable vehicle.

In other methods based on pretargeting techniques, a multispecific antibody or fusion protein may comprise an anti- CD19 antibody as described herein, attached to at least one other antibody or fragment that binds to a hapten, such as an HSG hapten. The hapten may be incorporated into a targetable conjugate that comprises one or more therapeutic and/or diagnostic agents. The multispecific antibody or fusion protein may be administered to a subject and allowed to bind to a target antigen, such as CD19, expressed on a target cell, such as a B cell. After allowing a sufficient amount of time for non-bound circulating antibody to be removed from circulation, the targetable conjugate may be administered, which then binds to the multispecific antibody or fusion protein localized to the target cell or tissue. Such pretargeting methods improve the therapeutic index by preferential delivery of therapeutic agent to the target cell or tissue compared to normal cells or tissues. Methods of pretargeting are well known in the art (see, e.g., U.S. Pat. Nos. 6,361,774; 6,962,702; 7,074,403; 7,201,890; 7,230,084; 7,230,085 and 7,429,381, each incorporated herein by reference in its entirety.)

The therapeutic methods can further be supplemented with the administration to the subject concurrently or sequentially of a therapeutically effective amount of at least one therapeutic agent, formulated in a pharmaceutically acceptable vehicle, wherein the therapeutic agent is preferably a cytotoxic agent, a radioactive label, an immunomodulator, a hormone, a photoactive therapeutic agent or a combination thereof, formulated in a pharmaceutically acceptable vehicle.

Further, the antibody fusion proteins can be administered to a subject concurrently or sequentially with a therapeutically effective amount of a therapeutic conjugate comprising at least one MAb bound to at least one therapeutic agent, wherein said MAb component of the conjugate preferably comprises at least one humanized, chimeric, human or murine (for non-human subjects) MAb selected from the group consisting of a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, HLA-DR, tenascin, VEGF, PlGF, ED-B fibronectin, an oncogene, an oncogene product, CD66a-d, necrosis antigens, Ii, IL-2, IL-6, T101, TAC, IL-6, TRAIL-R1 (DR4) and TRAIL-R2 (DR5) formulated in a pharmaceutically acceptable vehicle. The antibody fusion protein itself can be conjugated to a therapeutic agent and thus provides a vehicle to attach more than one therapeutic agent to an antibody component and these therapeutic agents can be a combination of different recited agents or combinations of the same agents, such as two different therapeutic radioactive labels.

Also encompassed are methods of diagnosing or detecting a B-cell lymphoma or leukemia or autoimmune disease in a subject comprising administering to the subject, such as a mammal, including humans and domestic and companion pets, such as dogs, cats, rabbits, guinea pigs, a diagnostic conjugate comprising an anti-CD19 MAb or fragment thereof or an antibody fusion protein or fragment thereof that binds to the lymphoma, leukemia or autoimmune cell, wherein the anti-CD19 MAb or fragment thereof or antibody fusion protein or fragment thereof is bound to at least one diagnostic agent, formulated in a pharmaceutically acceptable vehicle. Useful diagnostic agents are described herein.

Antibody Preparation

Monoclonal antibodies (MAbs) are a homogeneous population of antibodies to a particular antigen wherein the antibody comprises only one type of antigen binding site and binds to only one epitope on an antigenic determinant. Rodent monoclonal antibodies to specific antigens may be obtained by methods known to those skilled in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into human variable domains attached to human constant region sequences, and then, substituting selected human residues in the framework regions with their murine counterparts. Preferred FR residues for substitution include those FR residues that are located near or touching the CDR residues, as well as residues that affect the stability and/or expression levels of the antibody. The use of antibody components derived from humanized monoclonal antibodies obviates potential problems associated with the immunogenicity of murine constant regions.

General techniques for cloning murine immunoglobulin variable domains are disclosed, for example, by the publication of Orlandi et al., Proc. Natl. Acad. Sci. USA 86: 3833 (1989), which is incorporated by reference in its entirety. Techniques for constructing chimeric antibodies are well known to those of skill in the art. As an example, Leung et at., Hybridoma 13:469 (1994), produced an LL2 chimera by combining DNA sequences encoding the Vk and VH domains of LL2 monoclonal antibody, an anti-CD22 antibody, with respective human and IgG1 constant region domains. This publication also provides the nucleotide sequences of the LL2 light and heavy chain variable regions, Vk and VH, respectively. Techniques for producing humanized MAbs are described, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993), each of which is incorporated herein by reference.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric MAb with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988).

Another method for producing the antibodies is by production in the milk of transgenic livestock. See, e.g., Colman, A., Biochem. Soc. Symp., 63: 141-147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors which contain a promoter sequence that is preferentially expressed in mammary epithelial cells. Examples include, but are not limited to, promoters from rabbit, cow and sheep casein genes, the cow-lactoglobulin gene, the sheep-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A fully human antibody, i.e., human anti-CD19 MAbs or other human antibodies, such as anti-CD22, anti-CD23, anti-CD20, anti-CD74 or anti-CD21 MAbs, can be obtained from a transgenic non-human animal. See, e.g., Mendez et al., Nature Genetics, 15: 146-156 (1997); U.S. Pat. No. 5,633,425, which are incorporated in their entirety by reference. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Further recent methods for producing bispecific MAbs include engineered recombinant MAbs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bispecific fusion proteins can be produced using molecular engineering. See, for example, Alt et al., FEBS Lett. 454:90-4 (1999), which is incorporated herein by reference in its entirety. In one form, the bispecific fusion protein consists of, for example, a scFv with a single binding site for one antigen and a Fab fragment with a single binding site for a second antigen. In another form, the bispecific fusion protein consists of, for example, an IgG with two binding sites for one antigen and two scFv with two binding sites for a second antigen.

Bispecific fusion proteins linking two or more different single-chain antibodies or antibody fragments are produced in similar manner. Recombinant methods can be used to produce a variety of fusion proteins. For example a fusion protein comprising a Fab fragment derived from a humanized monoclonal anti-CD19 antibody and a scFv derived from a murine anti-diDTPA can be produced. A flexible linker, such as GGGS connects the scFv to the constant region of the heavy chain of the anti-CD19 antibody. Alternatively, the scFv can be connected to the constant region of the light chain of another humanized antibody. Appropriate linker sequences necessary for the in-frame connection of the heavy chain Fd to the scFv are introduced into the VL and Vk domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an anti-CD19 antibody. The resulting vector can be used to transfect an appropriate host cell, such as a mammalian cell for the expression of the bispecific fusion protein.

More recently, a novel technique known as dock-and-lock (DNL) has been developed to provide for the highly efficient formation of constructs comprising virtually any combination of peptide or protein effectors (see, e.g., U.S. Patent Application Publ. Nos. 20060228357; 20060228300; 20070086942; 20070140966 and 20070264265, each incorporated herein by reference in its entirety). In various permutations, the constructs are not limited to protein or peptide effectors, but may comprise other types of effector agents that may be attached to proteins or peptides, such as chemotherapeutic agents. The technique utilizes complementary protein binding domains, referred to as anchoring domains and dimerization and docking domains, which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies, either as naked antibody moieties or in combination with a wide range of other effector molecules such as immunomodulators, enzymes, chemotherapeutic agents, chemokines, cytokines, diagnostic agents, therapeutic agents, radionuclides, imaging agents, anti-angiogenic agents, growth factors, oligonucleotides, hormones, peptides, toxins, pro-apoptotic agents, or a combination thereof. Any of the techniques known in the art for making bispecific or multispecific antibodies may be utilized in the practice of the presently claimed methods.

Known Antibodies

In certain embodiments, for example those involving bispecific or multispecific antibodies incorporating an anti-CD19 antibody and another antibody against a different antigenic target, it may be preferred to utilize a commercially available or publicly known antibody, rather than making one de novo. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, incorporated herein by reference with respect to antibody variable region and/or CDR sequences and/or ATCC Accession Numbers for antibody-producing hybridoma cell lines. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Production of Antibody Fragments

Antibody fragments which recognize specific epitopes can be generated by known techniques. The antibody fragments are antigen binding portions of an antibody, such as F(ab')$_2$, Fab', F(ab)$_2$, Fab, Fv, sFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991), each incorporated herein by reference.

An antibody fragment can be prepared by proteolytic hydrolysis of the full-length antibody or by expression in *E. coli* or another host of the DNA coding for the fragment. An antibody fragment can be obtained by pepsin or papain digestion of full length antibodies by conventional methods. For example, an antibody fragment can be produced by enzymatic cleavage of antibodies with pepsin to provide a 5S fragment denoted F(ab)$_2$. This fragment can be further cleaved using a thiol reducing agent, and optionally a blocking group for the sulfhydryl groups resulting from cleavage of disulfide linkages, to produce 3.5S Fab monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, incorporated herein in their entireties by reference. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBOD- IES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the same antigen that is recognized by the intact antibody.

Multispecific and Multivalent Antibodies

The anti-CD19 antibodies, as well as other antibodies with different specificities for use in combination therapy, can also be made as multispecific antibodies, comprising at least one binding site to a CD19 epitope or antigen and at least one binding site to another epitope on CD19 or another antigen, or multivalent antibodies, comprising multiple binding sites to the same epitope or antigen.

A bispecific antibody or antibody fragment may have at least one binding region that specifically binds a targeted cell marker and at least one other binding region that specifically binds a targetable conjugate. The targetable conjugate comprises a carrier portion which comprises or bears at least one epitope recognized by at least one binding region of the bispecific antibody or antibody fragment. A variety of recombinant methods can be used to produce bispecific antibodies and antibody fragments as described above.

An anti-CD19 multivalent antibody is also contemplated. This multivalent target binding protein is constructed by association of a first and a second polypeptide. The first polypeptide comprises a first single chain Fv molecule covalently linked to a first immunoglobulin-like domain which preferably is an immunoglobulin light chain variable region domain. The second polypeptide comprises a second single chain Fv molecule covalently linked to a second immunoglobulin-like domain which preferably is an immunoglobulin heavy chain variable region domain. Each of the first and second single chain Fv molecules forms a target binding site, and the first and second immunoglobulin-like domains associate to form a third target binding site.

A single chain Fv molecule with the VL-L-VH configuration, wherein L is a linker, may associate with another single chain Fv molecule with the VH-L-VL configuration to form a bivalent dimer. In this case, the VL domain of the first scFv and the VH domain of the second scFv molecule associate to form one target binding site, while the VH domain of the first scFv and the VL domain of the second scFv associate to form the other target binding site.

Another embodiment is an anti-CD19 bispecific, trivalent targeting protein comprising two heterologous polypeptide chains associated noncovalently to form three binding sites, two of which have affinity for one target and a third which has affinity for a hapten that can be made and attached to a carrier for a diagnostic and/or therapeutic agent. Preferably, the binding protein has two CD19 binding sites and one CD22 binding site. The bispecific, trivalent targeting agents have two different scFvs, one scFv contains two VH domains from one antibody connected by a short linker to the VL domain of another antibody and the second scFv contains two VL domains from the first antibody connected by a short linker to the VH domain of the other antibody. The methods for generating multivalent, multispecific agents from VH and VL domains provide that individual chains synthesized from a DNA plasmid in a host organism are composed entirely of VH domains (the VH-chain) or entirely of VL domains (the VL-chain) in such a way that any agent of multivalency and multispecificity can be produced by non-covalent association of one VH-chain with one VL-chain. For example, forming a trivalent, trispecific agent, the VH-chain will consist of the amino acid sequences of three VH domains, each from an antibody of different specificity, joined by peptide linkers of variable lengths, and the VL-chain will consist of complementary VL domains, joined by peptide linkers similar to those used for the VH-chain. Since the VH and VL domains of antibodies associate in an anti-parallel fashion, the preferred method in this invention has the VL domains in the VL-chain arranged in the reverse order of the VH domains in the VH-chain.

Diabodies, Triabodies and Tetrabodies

The anti-CD19 antibodies can also be used to prepare functional bispecific single-chain antibodies (bsAb), also called diabodies, and can be produced in mammalian cells using recombinant methods. See, e.g., Mack et al., Proc. Natl. Acad. Sci., 92: 7021-7025, 1995, incorporated herein by reference. For example, bsAb are produced by joining two single-chain Fv fragments via a glycine-serine linker using recombinant methods. The V light-chain (VL) and V heavy-chain (VH) domains of two antibodies of interest are isolated using standard PCR methods. The VL and VH cDNAs obtained from each hybridoma are then joined to form a single-chain fragment in a two-step fusion PCR. The first PCR step introduces the $(Gly-4-Ser1)_3$ linker, and the second step joins the VL and VH amplicons. Each single chain molecule is then cloned into a bacterial expression vector. Following amplification, one of the single-chain molecules is excised and sub-cloned into the other vector, containing the second single-chain molecule of interest. The resulting bsAb fragment is subcloned into a eukaryotic expression vector. Functional protein expression can be obtained by transfecting the vector into CHO cells, Sp2/0 cells or Sp-EEE cells. Bispecific fusion proteins are prepared in a similar manner.

For example, a humanized, chimeric or human anti-CD19 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the VH polypeptide of the humanized anti-CD19 MAb connected to the VK polypeptide of the humanized anti-CD19 MAb by a five amino acid residue linker are utilized. Each chain forms one half of the humanized anti-CD19 diabody. In the case of triabodies, the three chains comprising VH polypeptide of the humanized anti-CD19 MAb connected to the VK polypeptide of the humanized anti-CD19 MAb by no linker are utilized. Each chain forms one third of the hCD19 triabody.

The ultimate use of the bispecific diabodies described herein is for pretargeting CD19 positive tumors for subsequent specific delivery of diagnostic or therapeutic agents. These diabodies bind selectively to targeted antigens allowing for increased affinity and a longer residence time at the desired location. Moreover, non-antigen bound diabodies are cleared from the body quickly and exposure of normal tissues is minimized. Bispecific antibody point mutations for enhancing the rate of clearance can be found in U.S. Provisional Application No. 60/361,037, which is incorporated herein by reference in its entirety. Bispecific diabodies for affinity enhancement are disclosed in U.S. application Ser. No. 10/270,071, Ser. No. 10/270,073 and Ser. No. 10/328,190, which are incorporated herein by reference in their entirety.

The diagnostic and therapeutic agents can include isotopes, drugs, toxins, cytokines, hormones, enzymes, oligonucleotides, growth factors, conjugates, radionuclides, and metals. For example, gadolinium metal is used for magnetic resonance imaging (MRI). Examples of radio nuclides are $^{225}$Ac, $^{18}$F, $^{68}$Ga, $^{67}$Ga, $^{90}$Y, $^{86}$Y, $^{111}$In, $^{131}$I, $^{125}$I, $^{123}$I, $^{99m}$Tc, $^{94m}$Tc, $^{186}$Re, $^{188}$Re, $^{177}$Lu, $^{62}$Cu, $^{64}$Cu, $^{67}$Cu, $^{212}$Bi, $^{213}$Bi, $^{32}$P, $^{11}$C, $^{13}$N, $^{15}$O, $^{76}$Br, and $^{211}$At. Other radionuclides are also available as diagnostic and therapeutic agents, especially those in the energy range of 60 to 4,000 keV.

More recently, a tetravalent tandem diabody (termed tandab) with dual specificity has been reported (Cochlovius et al., Cancer Research (2000) 60: 4336-4341). The bispecific tandab is a dimer of two identical polypeptides, each containing four variable domains of two different antibodies (VH1, VL1, VH2, VL2) linked in an orientation to facilitate the formation of two potential binding sites for each of the two different specificities upon self-association.

Conjugated Anti-CD19 Antibodies

Another embodiment concerns conjugated anti-CD19 antibodies. Compositions and methods for multivalent, multispecific agents are described in U.S. Patent Application Ser. No. 60/436,359, filed Dec. 24, 2002, and U.S. Patent Application Ser. No. 60/464,532, filed Apr. 23, 2003, which are incorporated herein by reference in their entirety.

Additional amino acid residues may be added to either the N- or C-terminus of the polypeptide. The additional amino acid residues may comprise a peptide tag, a signal peptide, a cytokine, an enzyme (for example, a pro-drug activating enzyme), a hormone, a peptide toxin, such as pseudomonas exotoxin, a peptide drug, a cytotoxic protein or other functional proteins. As used herein, a functional protein is a protein which has a biological function.

In one embodiment, drugs, toxins, radioactive compounds, enzymes, hormones, oligonucleotides, cytotoxic proteins, chelates, cytokines and other functional agents may be conjugated to the target binding protein, preferably through covalent attachments to the side chains of the amino acid residues of the target binding protein, for example amine, carboxyl, phenyl, thiol or hydroxyl groups. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the binding protein preferably does not significantly affect the protein's binding specificity or affinity to its target. As used herein, a functional agent is an agent which has a biological function. A preferred functional agent is a cytotoxic agent.

As discussed above, enzymes are also useful therapeutic agents. For example, alkaline phosphatase for use in combination with phosphate-containing prodrugs (U.S. Pat. No. 4,975,278); arylsulfatase for use in combination with sulfate-containing prodrugs (U.S. Pat. No. 5,270,196); peptidases and proteases, such as *serratia* protease, thermolysin, subtilisin, carboxypeptidase (U.S. Pat. Nos. 5,660,829; 5,587,161; 5,405,990) and cathepsins (including cathepsin B and L), for use in combination with peptide-based prodrugs; D-alanylcarboxypeptidases for use in combination with D-amino acid-modified prodrugs; carbohydrate-cleaving enzymes such as beta-galactosidase and neuraminidase for use in combination with glycosylated prodrugs (U.S. Pat. Nos. 5,561, 119; 5,646,298); beta-lactamase for use in combination with beta-lactam-containing prodrugs; penicillin amidases, such as penicillin-V-amidase (U.S. Pat. No. 4,975,278) or penicillin-G-amidase, for use in combination with drugs derivatized at their amino nitrogens with phenoxyacetamide or phenylacetamide groups; and cytosine deaminase (U.S. Pat. Nos. 5,338,678; 5,545,548) for use in combination with 5-fluorocytosine-based prodrugs (U.S. Pat. No. 4,975,278), are suitable therapeutic agents.

In still other embodiments, bispecific antibody-directed delivery of therapeutics or prodrug polymers to in vivo targets can be combined with bispecific antibody delivery of radionuclides, such that combination chemotherapy and radioimmunotherapy is achieved. Each therapy can be conjugated to the targetable conjugate and administered simultaneously, or the nuclide can be given as part of a first targetable conjugate and the drug given in a later step as part of a second targetable conjugate.

In another embodiment, cytotoxic agents may be conjugated to a polymeric carrier, and the polymeric carrier may subsequently be conjugated to the multivalent target binding protein. For this method, see Ryser et al., Proc. Natl. Acad. Sci. USA, 75:3867-3870, 1978, U.S. Pat. No. 4,699,784 and U.S. Pat. No. 4,046,722, which are incorporated herein by reference. Conjugation preferably does not significantly affect the binding specificity or affinity of the binding protein.

Humanized, Chimeric and Human Antibodies for Treatment and Diagnosis

Humanized, chimeric and human monoclonal antibodies, i.e., anti-CD19 MAbs and other MAbs described herein, are suitable for use in therapeutic methods and diagnostic methods. Accordingly, the present invention contemplates the administration of the humanized, chimeric and human antibodies alone as a naked antibody or administered as a multimodal therapy, temporally according to a dosing regimen, but not conjugated to, a therapeutic agent. The efficacy of the naked anti-CD19 MAbs can be enhanced by supplementing naked antibodies with one or more other naked antibodies, i.e., MAbs to specific antigens, such as CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, HLA-DR, tenascin, VEGF, P1GF, ED-B fibronectin, an oncogene, an oncogene product, CD66a-d, necrosis antigens, Ii, IL-2, T101, TAC, IL-6, TRAIL-R1 (DR4) and TRAIL-R2 (DR5) with one or more immunoconjugates of anti-CD19, or antibodies to theses recited antigens, conjugated with therapeutic agents, including drugs, toxins, immunomodulators, hormones, enzymes, oligonucleotides, therapeutic radionuclides, etc., with one or more therapeutic agents, including drugs, toxins, enzymes, oligonucleotides, immunomodulators, hormones, therapeutic radionuclides, etc., administered concurrently or sequentially or according to a prescribed dosing regimen, with the MAbs.

Preferred B-cell antigens include those equivalent to human CD19, CD20, CD21, CD22, CD23, CD46, CD52, CD74, CD80, and CD5 antigens. Preferred T-cell antigens include those equivalent to human CD4, CD8 and CD25 (the IL-2 receptor) antigens. An equivalent to HLA-DR antigen can be used in treatment of both B-cell and T-cell disorders. Particularly preferred B-cell antigens are those equivalent to human CD19, CD20, CD22, CD21, CD23, CD74, CD80, and HLA-DR antigens. Particularly preferred T-cell antigens are those equivalent to human CD4, CD8 and CD25 antigens. CD46 is an antigen on the surface of cancer cells that block complement-dependent lysis (CDC).

Further, the present invention contemplates the administration of an immunoconjugate for diagnostic and therapeutic uses in B cell lymphomas and other disease or disorders. An immunoconjugate, as described herein, is a molecule comprising an antibody component and a therapeutic or diagnostic agent, including a peptide which may bear the diagnostic or therapeutic agent. An immunoconjugate retains the immunoreactivity of the antibody component, i.e., the antibody moiety has about the same or slightly reduced ability to bind the cognate antigen after conjugation as before conjugation.

A wide variety of diagnostic and therapeutic reagents can be advantageously conjugated to the claimed antibodies. The therapeutic agents recited here are those agents that also are useful for administration separately with the naked antibody as described above. Therapeutic agents include, for example, chemotherapeutic drugs such as vinca alkaloids, anthracyclines, epidophyllotoxins, taxanes, antimetabolites, alkylating agents, antibiotics, COX-2 inhibitors, antimitotics, anti-angiogenic and apoptotic agents, particularly doxorubicin, methotrexate, taxol, CPT-11, camptothecans, proteosome inhibitors, and others from these and other classes of anticancer agents, thalidomide and derivates, oligonucleotides, particularly antisense and RNAi oligonucleotides (e.g., against bcl-2), and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, enzymes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Additionally, a chelator such as DTPA, DOTA, TETA, or NOTA or a suitable peptide, to which a detectable label, such as a fluorescent molecule, or cytotoxic agent, such as a heavy metal or radionuclide, can be conjugated to the claimed antibodies. For example, a therapeutically useful immunoconjugate can be obtained by conjugating a photoactive agent or dye to an antibody composite. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, Chem. Britain 22:430 (1986).

Moreover, monoclonal antibodies have been coupled with photoactivated dyes for achieving phototherapy. Mew et al., J. Immunol. 130:1473 (1983); idem., Cancer Res. 45:4380 (1985); Oseroff et al., Proc. Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg Med. 9:422 (1989); Pelegrin et al., Cancer 67:2529 (1991). However, these earlier studies did not include use of endoscopic therapy applications, especially with the use of antibody fragments or subfragments. Thus, the present invention contemplates the therapeutic use of immunoconjugates comprising photo active agents or dyes.

Also contemplated by the present invention are the use of radioactive and non-radioactive agents as diagnostic agents. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference.

Furthermore, a radiolabeled antibody or immunoconjugate may comprise a gamma-emitting radioisotope or a positron-emitter useful for diagnostic imaging. Suitable radioisotopes, particularly in the energy range of 60 to 4,000 keV, include $^{131}I$, $^{123}I$, $^{124}I$, $^{86}Y$, $^{62}Cu$, $^{64}Cu$, $^{111}In$, $^{67}Ga$, $^{68}Ga$, $^{99m}Tc$, $^{94m}Tc$, $^{18}F$, $^{11}C$, $^{13}N$, $^{15}O$, $^{75}Br$, and the like. See for example, U.S. Provisional Application No. 60/342,104, which discloses positron emitters, such as $^{18}F$, $^{68}Ga$, $^{94m}Tc$ and the like, for imaging purposes and which is incorporated in its entirety by reference.

A toxin, such as *Pseudomonas* exotoxin, may also be complexed to or form the therapeutic agent portion of an antibody fusion protein of an anti-CD19 antibody. Other toxins suitably employed in the preparation of such conjugates or other fusion proteins, include ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin. See, for example, Pastan et al., Cell 47:641 (1986), and Goldenberg, CA—A Cancer Journal for Clinicians 44:43 (1994). Additional toxins suitable for use in the present invention are known to those of skill in the art and are disclosed in U.S. Pat. No. 6,077,499, which is incorporated in its entirety by reference.

An immunomodulator, such as a cytokine may also be conjugated to, or form the therapeutic agent portion of an antibody fusion protein or be administered with the humanized anti-CD19 antibodies. Suitable cytokines for the present invention include, but are not limited to, interferons and interleukins, as described below.

Preparation of Immunoconjugates

Any of the antibodies or antibody fusion proteins can be conjugated with one or more therapeutic or diagnostic agents. Generally, one therapeutic or diagnostic agent is attached to each antibody or antibody fragment but more than one therapeutic agent or diagnostic agent can be attached to the same antibody or antibody fragment. The antibody fusion proteins may comprise two or more antibodies or fragments thereof and each of the antibodies that compose this fusion protein can contain a therapeutic agent or diagnostic agent. Additionally, one or more of the antibodies of the antibody fusion protein can have more than one therapeutic of diagnostic agent attached. Further, the therapeutic agents do not need to be the same but can be different therapeutic agents. For example, one can attach a drug and a radioisotope to the same fusion protein. Particularly, an IgG can be radiolabeled with $^{131}I$ and attached to a drug. The $^{131}I$ can be incorporated into the tyrosine of the IgG and the drug attached to the epsilon amino group of the IgG lysines. Both therapeutic and diagnostic agents also can be attached to reduced SH groups and to the carbohydrate side chains.

Bispecific antibodies are useful in pretargeting methods and provide a preferred way to deliver therapeutic agents or diagnostic agents to a subject. U.S. Ser. No. 09/382,186 discloses a method of pretargeting using a bispecific antibody, in which the bispecific antibody is labeled with $^{125}I$ and delivered to a subject, followed by a divalent peptide labeled with $^{99m}Tc$. Pretargeting methods are also described in U.S. Ser. No. 09/823,746 (Hansen et al.) and Ser. No. 10/150,654 (Goldenberg et al.), which are incorporated herein by reference in their entirety. The delivery results in excellent tumor/normal tissue ratios for $^{125}I$ and $^{99m}Tc$. Any combination of known therapeutic agents or diagnostic agents can be used to label the antibodies and antibody fusion proteins. The binding specificity of the antibody component of the MAb conjugate, the efficacy of the therapeutic agent or diagnostic agent and the effector activity of the Fc portion of the antibody can be determined by standard testing of the conjugates.

A therapeutic or diagnostic agent can be attached at the hinge region of a reduced antibody component via disulfide bond formation. As an alternative, such peptides can be attached to the antibody component using a heterobifunctional crosslinker, such as N-succinyl 3-(2-pyridyldithio) proprionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

Alternatively, the therapeutic or diagnostic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region is absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); Hansen et al., U.S. Pat. No. 5,443,953 (1995), Leung et al., U.S. Pat. No. 6,254,868, all of which are incorporated in their entirety by reference. The engineered carbohydrate moiety is used to attach the therapeutic or diagnostic agent.

Pharmaceutically Acceptable Excipients

The humanized, chimeric and human anti-CD19 MAbs to be delivered to a subject can consist of the MAb alone, immunoconjugate, fusion protein, or can comprise one or more pharmaceutically suitable excipients, one or more additional ingredients, or some combination of these.

The immunoconjugate or naked antibody can be formulated according to known methods to prepare pharmaceutically useful compositions, whereby the immunoconjugate or naked antibody are combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., Bio/Technology 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, antibody fusion proteins, or naked antibody may also be administered to a mammal subcutaneously or even by other parenteral routes. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

For purposes of therapy, the immunoconjugate, fusion protein, or naked antibody is administered to a mammal in a therapeutically effective amount. A suitable subject is usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation is physiologically significant if its presence invokes an antitumor response or mitigates the signs and symptoms of an autoimmune disease state. A physiologically significant effect could also be the evocation of a humoral and/or cellular immune response in the recipient mammal.

Methods of Treatment

The present invention contemplates the use of naked or conjugated anti-CD19 antibodies as the primary composition for treatment of B cell disorders and other diseases. In particular, the compositions described herein are particularly useful for treatment of various autoimmune diseases as well as indolent forms of B-cell lymphomas, aggressive forms of B-cell lymphomas, chronic lymphatic leukemias, acute lymphatic leukemias, and Waldenstrom's macroglobulinemia. For example, the humanized anti-CD19 antibody components and immunoconjugates can be used to treat both indolent and aggressive forms of non-Hodgkin's lymphoma.

As discussed above, the antibodies are also suitable for diagnosis and treatment of various autoimmune diseases. Such diseases include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, and fibrosing alveolitis. The most common treatments for such diseases are corticosteroids and cytotoxic drugs, which can be very toxic. These drugs also suppress the entire immune system, can result in serious infection, and have adverse effects on the bone marrow, liver and kidneys. Other therapeutics that have been used to treat Class III autoimmune diseases to date have been directed against T-cells and macrophages.

The compositions for treatment contain at least one humanized, chimeric or human monoclonal anti-CD19 antibody alone or in combination with other antibodies, such as other humanized, chimeric, or human antibodies, therapeutic agents or immunomodulators. In particular, combination therapy with a fully human antibody is contemplated.

Naked or conjugated antibodies to the same or different epitope or antigen may also be used in combination. For example, a humanized, chimeric or human naked anti-CD19 antibody may be combined with another naked humanized, chimeric or human anti-CD19 or with a naked anti-CD20, anti-CD22 or other B-cell lineage antibody. A humanized, chimeric or human naked anti-CD19 antibody may be combined with an anti-CD19 immunoconjugate or anti-CD22 radioconjugate. An anti-CD22 naked antibody may be combined with a humanized, chimeric or human anti-CD19 antibody conjugated to an isotope, one or more chemotherapeutic agents, cytokines, toxins or a combination thereof. A fusion protein of a humanized, chimeric or human anti-CD19 antibody and a toxin or immunomodulator, or a fusion protein of at least two different B-cell antibodies (e.g., an anti-CD19 and an anti-CD22 MAb or an anti-CD19 and an anti-CD20 MAb) may also be used. Many different antibody combinations, targeting at least two different antigens associated with B-cell disorders, as listed above, may be constructed, either as naked antibodies or conjugated with a therapeutic agent or immunomodulator, or merely in combination with another therapeutic agent, such as a cytotoxic drug, a cytokine or radionuclide.

As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-21 and IL-18), colony stimulating factors (e.g., granulocyte-colony stimulating factor (G-CSF) and granulocyte macrophage-colony stimulating factor (GM-CSF)), interferons (e.g., interferons-alpha, -beta and -gamma), the stem cell growth factor designated "S1 factor," erythropoietin and thrombopoietin. Examples of suitable immunomodulator moieties include IL-2, IL-6, IL-10, IL-12, IL-18, IL-21, interferon, TNF, and the like. Alternatively, subjects can receive naked anti-CD19 antibodies and a separately administered cytokine, which can be administered before, concurrently with or after administration of the naked anti-CD19 antibodies. As discussed supra, the anti-CD19 antibody may also be conjugated to the immunomodulator. The immunomodulator may also be conjugated to a hybrid antibody consisting of one or more antibodies binding to different antigens.

Multimodal therapies further include immunotherapy with naked anti-CD19 antibodies supplemented with administration of antibodies that bind CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, HLA-DR (including the invariant chain), tenascin, VEGF, P1GF, ED-B fibronectin, an oncogene, an oncogene product, CD66a-d, necrosis antigens, Ii, IL-2, T101, TAC, IL-6, TRAIL-R1 (DR4) and TRAIL-R2 (DR5) in the form of naked antibodies, fusion proteins, or as immunoconjugates. These antibodies include polyclonal, monoclonal, chimeric, human or humanized antibodies that recognize at least one epitope on these antigenic determinants. Anti-CD19 and anti-CD22 antibodies are known to those of skill in the art. See, for example, Ghetie et al., Cancer Res. 48:2610 (1988); Hekman et al., Cancer Immunol. Immunother. 32: 364 (1991); Longo, Curr. Opin. Oncol. 8:353 (1996) and U.S. Pat. Nos. 5,798,554 and 6,187,287, incorporated in their entirety by reference. Immunotherapy of autoimmune disorders with B-cell antibodies is described in the art. See, for example, WO0074718A1, which is incorporated herein by reference in its entirety.

In another form of multimodal therapy, subjects receive naked anti-CD19 antibodies, and/or immunoconjugates, in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., Eur. J. Haematol. 51:18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2027-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and bryostatin-1. Antisense bc1-2 oligonucleotide is also in clinical trials as a therapeutic for certain malignancies, including B-cell tumors. In a preferred multimodal therapy, both chemotherapeutic drugs and cytokines are co-administered with an antibody, immunoconjugate or fusion protein. The cytokines, chemotherapeutic drugs and antibody or immunoconjugate can be administered in any order, or together.

In a preferred embodiment, NHL is treated with 4 weekly infusions of the humanized anti-CD19 antibody at a dose of 200-400 mg/m² weekly for 4 consecutive weeks (iv over 2-8 hours), repeated as needed over next months/yrs. Also preferred, NHL is treated with 4 weekly infusions as above, but combined with epratuzumab (anti-CD22 humanized antibody) on the same days, at a dose of 360 mg/m², given as iv infusion over 1 hour, either before, during or after the anti-CD19 monoclonal antibody infusion. Still preferred, NHL is treated with 4 weekly infusions of the anti-CD19 antibody as above, combined with one or more injections of anti-CD22 MAb radiolabeled with a therapeutic isotope such as yttrium-90 (at dose of Y-90 between 5 and 35 mCi/m² as one or more injections over a period of weeks or months. Anti-CD19 MAb may also be combined, in similar regimens, with anti-CD20 MAbs, such as the hA20 humanized MAb (U.S. application Ser. No. 10/366,709, filed Feb. 14, 2003), whereby a weekly dosex4 weeks per cycle, with optional repeated cycles, is given of each antibody at an individual dose of 250 mg/m² i.v. in combination. Either or both antibodies can also be given by s.c. injection, whereby a similar dose is given every other week, particularly for the therapy of patients with autoimmune disease.

In addition, a therapeutic composition can contain a mixture or hybrid molecules of monoclonal naked anti-CD19 antibodies directed to different, non-blocking CD19 epitopes. Accordingly, the present invention contemplates therapeutic compositions comprising a mixture of monoclonal anti-CD19 antibodies that bind at least two CD19 epitopes.

Although anti-CD19 antibodies are the primary therapeutic compositions for treatment of B cell lymphoma and autoimmune diseases, the efficacy of such antibody therapy can be enhanced by supplementing the naked antibodies, with supplemental agents, such as immunomodulators, like interferons, including IFN-alpha, IFN-beta and IFN-gamma, interleukins including IL-1, IL-2, IL-6, IL-12, IL-15, IL-18, IL-21, and cytokines including G-CSF and GM-CSF. Accordingly, the anti-CD19 antibodies can be combined not only with antibodies and cytokines, either as mixtures (given separately or in some predetermined dosing regimen) or as conjugates or fusion proteins to the anti-CD19 antibody, but also can be given as a combination with drugs. For example, the anti-CD19 antibody may be combined with CHOP as a 4-drug chemotherapy regimen. Additionally, a naked anti-CD19 antibody may be combined with a naked anti-CD22 antibody and/or naked anti-CD20 antibodies and CHOP or Fludarabine as a drug combination for NHL therapy. The supplemental therapeutic compositions can be administered before, concurrently or after administration of the anti-CD19 antibodies.

As discussed supra, the antibodies can be used for treating B cell lymphoma and leukemia, and other B cell diseases or disorders. The antibodies may be used for treating any disease or syndrome which involves unwanted or undesirable B-cell activity or proliferation. For example, anti-CD19 antibodies can be used to treat B-cell related autoimmune diseases, including Class III autoimmune diseases. The antibodies can also be used to treat B-cell diseases such as graft versus host disease, or for transplant immunosuppressive therapy.

Anti-CD19 antibodies may also induce apoptosis in cells expressing the CD19 antigen. Evidence of this induction is supported in the literature. For example, it was demonstrated that apoptosis could be induced using lymphoid cells that have Fc-receptors reactive with the IgG1-Fc of anti-CD19 MAbs that crosslinked. See Shan et al., Cancer Immunol. Immunother. 48(12):673-683 (2000). Further, it was reported that aggregates of a chimeric anti-CD19 MAb, i.e., homopolymers, induced apoptosis. See Ghetie et al., Blood 97(5): 1392-1398 (2000) and Ghetie et al., Proc. Natl. Acad. Sci. USA 94(14): 7509-7514 (1997). Enhancement of the pro-apoptotic activity of the antibodies may be achieved by simultaneous use of a pro-apoptotic agent, such as an agent that inhibits the activity of one or more members of the anti-apoptosis gene family bc1-2. Antisense and RNAi agents are particularly useful in this regard and can be directed to B cells by conjugation with anti-CD19 antibodies as described herein.

Antibodies specific to the CD19 surface antigen of B cells can be injected into a mammalian subject, which then bind to the CD19 cell surface antigen of both normal and malignant B cells. A mammalian subject includes humans and domestic animals, including pets, such as dogs and cats. The anti-CD19 MAbs, i.e., humanized, chimeric, human, and even murine anti-CD19 MAbs, can be used to treat the non-human mammalian subjects when there is a species crossreactivity for the CD19 antigen. See Examples 10 and 11, below. The murine MAbs, which are immunogenic in humans, are usually less immunogenic in non-human mammalian subjects. The anti-CD19 antibody bound to the CD19 surface antigen leads to the destruction and depletion of neoplastic B cells. Because both normal and malignant B cells express the CD19 antigen, the anti-CD19 antibody will result in B cell death. However, only normal B cells will repopulate and the malignant B cells will be eradicated or significantly reduced. Additionally, chemical agents or radioactive labels having the potential to destroy the tumor can be conjugated to the anti-CD19 antibody such that the agent is specifically targeted to the neoplastic B cells.

Expression Vectors

The DNA sequence encoding a humanized, chimeric or human anti-CD19 MAb can be recombinantly engineered into a variety of known host vectors that provide for replication of the nucleic acid. These vectors can be designed, using known methods, to contain the elements necessary for directing transcription, translation, or both, of the nucleic acid in a cell to which it is delivered. Known methodology can be used to generate expression constructs that have a protein-coding sequence operably linked with appropriate transcriptional/translational control signals. These methods include in vitro recombinant DNA techniques and synthetic techniques. For example, see Sambrook et al., 1989, MOLECULAR CLONING: A LABORATORY MANUAL, Cold Spring Harbor Laboratory (New York); Ausubel et al., 1997, CURRENT PROTOCOLS IN MOLECULAR BIOLOGY, John Wiley & Sons (New York).

Vectors suitable for use can be viral or non-viral. Particular examples of viral vectors include adenovirus, AAV, herpes simplex virus, lentivirus, and retrovirus vectors. An example of a non-viral vector is a plasmid. In a preferred embodiment, the vector is a plasmid.

An expression vector, as described herein, is a polynucleotide comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

Preferably, the expression vector comprises the DNA sequence encoding a humanized, chimeric or human anti-CD19 MAb, which includes both the heavy and the light chain variable and constant regions. However, two expression vectors may be used, with one comprising the heavy chain variable and constant regions and the other comprising the light chain variable and constant regions. Still preferred, the expression vector further comprises a promoter, a DNA sequence encoding a secretion signal peptide, a genomic sequence encoding a human IgG1 heavy chain constant region, an Ig enhancer element and at least one DNA sequence encoding a selectable marker.

Also contemplated herein is a method for expressing a humanized anti-CD19 MAb, comprising (i) linearizing at least one expression vector comprising a DNA sequence encoding a humanized, chimeric, or human anti-CD19 MAb, (ii) transfecting mammalian cells with at least one of said linearized vector, (iii) selecting transfected cells which express a marker gene, and (iv) identifying the cells secreting the humanized anti-CD19 MAb from the transfected cells.

Methods of Making Anti-CD19 Antibodies

In general, the Vk and VH sequences encoding an anti-CD19 MAb can be obtained by a variety of molecular cloning procedures, such as RT-PCR, 5'-RACE, and cDNA library screening. Specifically, the V genes of an anti-CD19 MAb can be cloned by PCR amplification from a cell that expresses a murine or chimeric anti-CD19 MAb and then sequenced. To confirm their authenticity, the cloned VL and VH genes can be expressed in cell culture as a chimeric Ab as described by Orlandi et al., (Proc. Natl. Acad. Sci., USA, 86: 3833 (1989)) which is incorporated by reference. Based on the V gene sequences, a humanized anti-CD19 MAb can then be designed and constructed as described by Leung et al. (Mol. Immunol., 32: 1413 (1995)), which is incorporated herein by reference. cDNA can be prepared from any known hybridoma line or transfected cell line producing a murine or chimeric anti-CD19 MAb by general molecular cloning techniques (Sambrook et al., Molecular Cloning, A laboratory manual, 2nd Ed (1989)). The VK sequence for the MAb may be amplified using the primers Vk1BACK and Vk1FOR (Orlandi et al., 1989) or the extended primer set described by Leung et al. (BioTechniques, 15: 286 (1993)), which is incorporated herein by reference, while VH sequences can be amplified using the primer pair VH1BACK/VH1FOR (Orlandi et al., 1989), or the primers annealing to the constant region of murine IgG described by Leung et al. (Hybridoma, 13:469 (1994)), which is incorporated herein by reference.

The PCR reaction mixtures containing 10 µl of the first strand cDNA product, 10 µl of 10×PCR buffer [500 mM KCl, 100 mM Tris-HCl (pH 8.3), 15 mM $MgCl_2$, and 0.01% (w/v) gelatin] (Perkin Elmer Cetus, Norwalk, Conn.), 250 µM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified VK and VH fragments can be purified on 2% agarose (BioRad, Richmond, Calif.). Similarly, the humanized V genes can be constructed by a combination of long oligonucleotide template syntheses and PCR amplification as described by Leung et al. (Mol. Immunol., 32: 1413 (1995)). See Example 3 for a method for the synthesis of an oligo A and an oligo B on an automated RNA/DNA synthesizer (Applied Biosystems, Foster City, Calif.) for use in constructing humanized V genes.

PCR products for VK can be subcloned into a staging vector, such as a pBR327-based staging vector, VkpBR, that contains an Ig promoter, a signal peptide sequence and convenient restriction sites to facilitate in-frame ligation of the VK PCR products. PCR products for VH can be subcloned into a similar staging vector, such as the pBluescript-based VHpBS. Individual clones containing the respective PCR products may be sequenced by, for example, the method of Sanger et al. (Proc. Natl. Acad. Sci., USA, 74: 5463 (1977)).

The expression cassettes containing the VK and VH, together with the promoter and signal peptide sequences can be excised from VKpBR and VHpBS, respectively, by double restriction digestion as HindIII-BamHI fragments. The VK and VH expression cassettes can then be ligated into appropriate expression vectors, such as pKh and pG1g, respectively (Leung et al., Hybridoma, 13:469 (1994)). The expression vectors can be co-transfected into an appropriate cell, e.g., myeloma Sp2/0-Ag14 or Sp-EEE, colonies selected for hygromycin resistance, and supernatant fluids monitored for production of a chimeric or humanized anti-CD19 MAb by, for example, an ELISA assay. Alternatively, the VK and VH expression cassettes can be assembled in the modified staging vectors, YKpBR2 and VHpBS2, excised as XbaI/BamHI and XhoI/BamHI fragments, respectively, and subcloned into a single expression vector, such as pdHL2, as described by Gilles et al. (J. Immunol. Methods 125:191 (1989)) and also shown in Losman et al., (Cancer, 80:2660 (1997)) for expression in cells. Another vector that is useful is the GS vector, as described in Barnes et al., Cytotechnology 32: 109-123 (2000), which is preferably expressed in the NS0 cell line and CHO cells. Other appropriate mammalian expression systems are described in Werner et al., Arzneim.-Forsch./Drug Res. 48(11), Nr. 8, 870-880 (1998).

Co-transfection and assay for antibody secreting clones by ELISA, can be carried out as follows. About 10 µg of VkpKh (light chain expression vector) and 20 µg of VHpG1g (heavy chain expression vector) can be used for the transfection of $5 \times 10^6$ SP2/0 myeloma cells by electroporation (BioRad, Richmond, Calif.) according to Co et al., J. Immunol., 148: 1149 (1992). Following transfection, cells may be grown in 96-well microtiter plates in complete HSFM medium (Life Technologies, Inc., Grand Island, N.Y.) at 37° C., 5% $CO_2$. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis.

Transfectoma clones that are positive for the secretion of chimeric or humanized heavy chain can be identified by ELISA assay. Briefly, supernatant samples (about. 100 µl) from transfectoma cultures are added in triplicate to ELISA microtiter plates precoated with goat anti-human (GAH)-IgG, F(ab')$_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch) are added to the wells, (100 µl of antibody stock diluted×$10^4$, supplemented with the unconjugated antibody to a final concentration of 1.0 µg/ml). Following an incubation of 1 h, the plates are washed, typically three times. A reaction solution, [100 µl, containing 167 µg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 µl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 µm membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 µl of 3 M Tris (pH 8.6), and protein concentrations determined The following are the nucleotide sequences of the primers used to prepare the anti-CD19 antibodies:

```
hA19VkA
                                    (SEQ ID NO: 24)
5'-ATCACTTGTA AGGCCAGCCA AAGTGTTGAT TATGATGGTG

ATAGTTATTT GAACTGGTAC CAGCAGATTC CAGGGAAAGC

ACCTAAATTG TTGATCTACG ATGCTTCGAA TCTAGTTTCT

GGTATC-3' hA19VkB
                                    (SEQ ID NO: 25)
5'-TGCTGACAGT GATATGTTGC AATGTCTTCT GGTTGAAGAG

AGCTGATGGT GAAAGTGTAA TCTGTCCCAG ATCCGCTGCC

AGAGAATCGA GGAGGGATAC CAGAAACTAG ATTCGAAGCA

TCGTA-3' hA19VkBack
                                    (SEQ ID NO: 26)
5'-TCCGACATCC AGCTGACCCA GTCTCCATCA TCTCTGAGCG

CATCTGTTGG AGATAGGGTC ACTATCACTT GTAAGGCCAG

CCAAAG-3' hA19VkFor
                                    (SEQ ID NO: 27)
5'-GCTCCTTGAG ATCTGTAGCT TGGTCCCTCC ACCGAACGTC

CACGGATCTT CAGTACTTTG CTGACAGTGA TATGTTGCAA-3' hA19VHA
                                    (SEQ ID NO: 28)
5'-CTGGCTACGC TTTCAGTAGC TACTGGATGA ACTGGGTGAG

GCAGAGGCCT GGACAGGGTC TTGAGTGGAT TGGACAGATT

TGGCCTGGAG ATGGTGATAC TAACTACAAT GGAAAGTTCA

AGGGGCGCGC CACTATT-3' hA19VHB
                                    (SEQ ID NO: 29)
5'-CGTAGTCTCC CGTCTTGCAC AAGAATAGAA CGCTGTGTCC

TCAGATCGTA GGCTGCTGAG TTCCATGTAG GCTGTATTAG

TGGATTCGTC GGCAGTAATA GTGGCGCGCC CCTTGAACTT

TCCATTGTA-3' hA19VHBack
                                    (SEQ ID NO: 30)
5'-CAGGTCCAAC TGCAGCAATC AGGGGCTGAA GTCAAGAAAC

CTGGGTCATCG GTGAAGGTCTC CTGCAAGGCT TCTGGCTACG

CTTTCAGTAG C-3' hA19VHFor
                                    (SEQ ID NO: 31)
5'-TGAGGAGACG GTGACCGTGG TCCCTTGGCC CCAGTAGTCC

ATAGCATAGT AATAACGGCC TACCGTCGTA GTCTCCCGTC

TTGCACAAG-3'
```

EXAMPLES

The invention is further described by reference to the following examples, which are provided for illustration only. The invention is not limited to the examples but rather includes all variations that are evident from the teachings provided herein.

Example 1

Construction of a Humanized Anti-CD19 Antibody

A chimeric A19 (cA19) antibody was constructed and expressed in Sp2/0 cell. The Vk (SEQ ID NO:1 and SEQ ID NO:3) and VH (SEQ ID NO:3 and SEQ ID NO:4) sequences of cA19 are shown in FIG. 1. The cA19 antibody was shown to bind to CD19+ human lymphoma cell lines, such as Raji, Daudi, and Ramos. The Ag-binding specificity of purified cA19 was evaluated by a cell surface competitive binding assay against other anti-CD19 antibodies, e.g. B4 (Coulter) and BU12 (Chembiochem). Briefly, varying concentrations of cA19 were incubated with Raji cells in the presence of a constant amount of an I-125 radiolabeled anti-CD19 antibody for 1 h. After washing to remove the unbound antibodies, the cell surface-bound radiolabeled antibody was quantitated by counting the cell pellets in a gamma counter. As shown in FIG. 2, cA19 competed with BU12 (Chembiochem) for cell surface binding, indicating these antibodies share similar or overlapping epitopes of the CD19 molecule.

The light chain and heavy chain variable region sequences encoding the humanized anti-hCD19 antibody (hA19) were designed and constructed. Comparison of the variable (V) region framework (FR) sequences of the cA19 (FIGS. 1A and 1B) to registered human antibodies in the Kabat database showed that the FRs of cA19 VK exhibited the highest degree of sequence homology to that of the human antibody REI (VK), while the VH sequence was most closely related with that of the human antibody EU (VH). The VH FR4 sequence of the human antibody NEWM, however, was better aligned with that of cA19 and used to replace the EU FR4 sequence for the humanization of the A19 heavy chain (FIG. 3B). Therefore, human REI framework sequences were used for Vk (FIG. 3A), and a combination of EU and NEWM framework sequences were used for VH (FIG. 3B). There are a number of amino acid changes in each chain outside of the CDR regions when compared to the starting human antibody frameworks. These residues are 4L, 39I, 58I, 60P, 87H, 100G, and 107K of VK (FIG. 3A) and 5Q, 27Y, 28A, 40R, 91S, 94R, 107T, and 108T of VH (FIG. 3B). The DNA and amino acid sequences of hA19 VK and VH are shown in FIGS. 4A and 4B, respectively.

Example 2

Method of hA19 Antibody Construction

To engineer the CDR-grafted hA19VH and VK genes, a modified strategy as described by Leung et al. (1995) was used to construct the designed VK and VH genes for hA19 using a combination of long oligonucleotide syntheses and PCR. Briefly, two long synthetic oligonucleotides (ca. 130 mer in length) representing the 5'-(sense strand, designated as A) and 3'-half (anti-sense strand, designated as B) of a V sequence are used as the templates in a PCR reaction. The 3'-terminal sequences of the long oligonucleotides A and B are designed to overlap and be complementary to each other. PCR is initiated by annealing of the 3'-termini of A and B to form a short double strand DNA flanked by the rest of long oligonucleotides (single strand). Each annealed end serves as a primer for the replication of the single stranded DNA, resulting in elongation of A and B to form the double-strand DNA. In the presence of two short oligonucleotide primers, V gene segment is generated by PCR amplification of the double strand DNA.

Heavy Chain

For the construction of hA19 VH domain, the long oligonucleotides, hA19VHA (SEQ ID NO:28, 126-mer) and hA19VHB (SEQ ID NO:29, 128-mer) were synthesized on an automated DNA synthesizer (Applied Biosystems). hA19VHA represents nt 74 to 126 of the hA19 VH domain, and hA19VHB represents the minus strand of the hA19VH domain complementary to nt 178 to 306. The 3'-terminal sequences (33 nt residues) of hA19VHA and VHB are complementary to each other. A minimal amount of hA19VHA and VHB (determined empirically) was amplified in the presence of 10 μl of 10×PCR Buffer (500 mM KCl, 100 mM Tris-HCl buffer, pH 8.3, 15 mM $MgCl_2$), 2 μmol of hA19VHBack (5'-CAGGTCCAAC TGCAGCAATC AGGGGCTGAA GTCAAGAAAC CTGGGTCATCG GTGAAGGTCTC CTGCAAGGCT TCTGGCTACG CTTTCAGTAG C-3' SEQ ID NO:30) and hA19VHF or (5'-TGAGGAGACG GTGACCGTGG TCCCTTGGCC CCAG-TAGTCC ATAGCATAGT AATAACGGCC TACCGTCGTA GTCTCCCGTC TTGCACAAG-3' SEQ ID NO:31), and 2.5 units of Taq DNA polymerase (Perkin Elmer Cetus, Norwalk, Conn.). The underlined portions are the restriction sites for subcloning as shown in FIG. 4B. This reaction mixture was subjected to three cycles of polymerase chain reaction (PCR) consisting of denaturation at 94° C. for 1 minute, annealing at 45° C. for 1 minute, and polymerization at 72° C. for 1.5 minutes. This procedure was followed by 27 cycles of PCR reaction consisting of denaturation at 94° C. for 1 minute, annealing at 55° C. for 1 minute, and polymerization at 72° C. for 1 minute. The resulting DNA fragment showed an expected molecular size in agarose gel electrophoresis. The double-stranded PCR-amplified product for hA19VH was gel-purified, restriction-digested with PstI and BstEII restriction enzymes and cloned into the complementary PstI/BstEII restriction sites of the heavy chain staging vector, VHpBS2, in which the VH sequence was fully assembled with the DNA sequence encoding the translation initiation codon and a secretion signal peptide in-frame ligated at the 5'-end and an intron sequence at the 3'-end. VHpBS2 is a modified staging vector of VHpBS (Leung et al., Hybridoma, 13:469 (1994)), into which a XhoI restriction site was introduced sixteen bases upstream of the translation initiation codon to facilitate the next subcloning step. The assembled VH gene was subcloned as a XhoI-BamHI restriction fragment into the expression vector, pdHL2, which contains the expression cassettes for both human IgG heavy and light chains under the control of IgH enhancer and MT1 promoter, as well as a mouse dhfr gene as a marker for selection and amplification (FIG. 4B). Since the heavy chain region of pdHL2 lacks a BamHI restriction site, this ligation requires use of a linker to provide a bridge between the BamHI site of the variable chain and the HindIII site present in the pdHL2 vector. The resulting expression vector was designated as hAI9VHpdHL2.

For constructing the full length DNA of the humanized VK sequence, hA19VkA (SEQ ID NO:24, 126-mer, represents nt 61 to 186 of the hA19 VK domain) and hA19VkB (SEQ ID NO:25, 124-mer, represents the minus strand of the hA19 VK domain complementary to nt 157 to 281) were synthesized as described above. hA19VkA and VkB were amplified by two short oligonucleotides hA19VkBack (5'-CAGGTCCAAC TGCAGCAATC AGGGGCTGAA GTCAAGAAAC CTGGGTCATCG GTGAAGGTCTC CTGCAAGGCT TCTGGCTACG CTTTCAGTAG C-3' SEQ ID NO:26) and hA19VkF or (5'-TGAGGAGACG GTGACCGTGG TCCCTTGGCC CCAGTAGTCC ATAGCATAGT AATAACGGCC TACCGTCGTA GTCTCCCGTC TTGCA-CAAG-3' SEQ ID NO:27) as described above. The underlined portions are restriction sites for subcloning as described below. Gel-purified PCR products for hA19 VK were restriction-digested with PvuII and BglII and cloned into the complementary PvuII/BclI sites of the light chain staging vector, VkpBR2. VkpBR2 is a modified staging vector of VkpBR (Leung et at, Hybridoma, 13:469 (1994)), into which a XbaI restriction site was introduced at sixteen bases upstream of the translation initiation codon. The assembled VK genes were subcloned as XbaI-BamHI restriction fragments into the expression vector containing the VH sequence, hA19VHpdHL2. The resulting expression vectors were designated as hA19pdHL2.

Example 3

Transfection and Expression of hA19 Antibodies

Approximately 30 μg of the expression vectors for hA19 were linearized by digestion with SalI and transfected into Sp2/0-Ag14 cells by electroporation (450V and 25 J-μF). The transfected cells were plated into 96-well plates for 2 days and then selected for drug-resistance by adding MTX into the medium at a final concentration of 0.075 μM. MTX-resistant colonies emerged in the wells after 2-3 weeks. Supernatants from colonies surviving selection were screened for human MAb secretion by ELISA assay. Briefly, 100 μl supernatants were added into the wells of a microtiter plate precoated with GAH-IgG, F(ab')$_2$ fragment-specific Ab and incubated for 1 h at room temperature. Unbound proteins were removed by washing three times with wash buffer (PBS containing 0.05% polysorbate 20). HRP-conjugated GAH-IgG, Fc fragment-specific Ab was added to the wells. Following an incubation of 1 h, the plate was washed. The bound HRP-conjugated Ab was revealed by reading A490 nm after the addition of a substrate solution containing 4 mM OPD and 0.04% H202. Positive cell clones were expanded and hB43 were purified from cell culture supernatant by affinity chromatography on a Protein A column.

Example 4

Determination of the Antigen-Binding Specificity and Affinity of Anti-CD19 Antibodies The Ag-binding specificity of cA19 and hA19 purified by affinity chromatography on a Protein A column were evaluated and compared by a cell surface competitive binding assay. Briefly, a constant amount (100,000 cpm, ~10 μCi/μg) of $^{125}$I-labeled cA19 or hA19 was incubated with Raji cells in the presence of varying concentrations (0.2-700 nM) of cA19 or hA19 at 4° C. for 1-2 h. Unbound Abs were removed by washing the cells in PBS. The radioactivity associated with cells was determined after washing. As shown in FIG. 2, the purified hA19 competed with $^{125}$I-labeled cA19 for cell surface binding and vice versa, indicating the apparent binding avidities are comparable between these two Abs.

Figure 5:
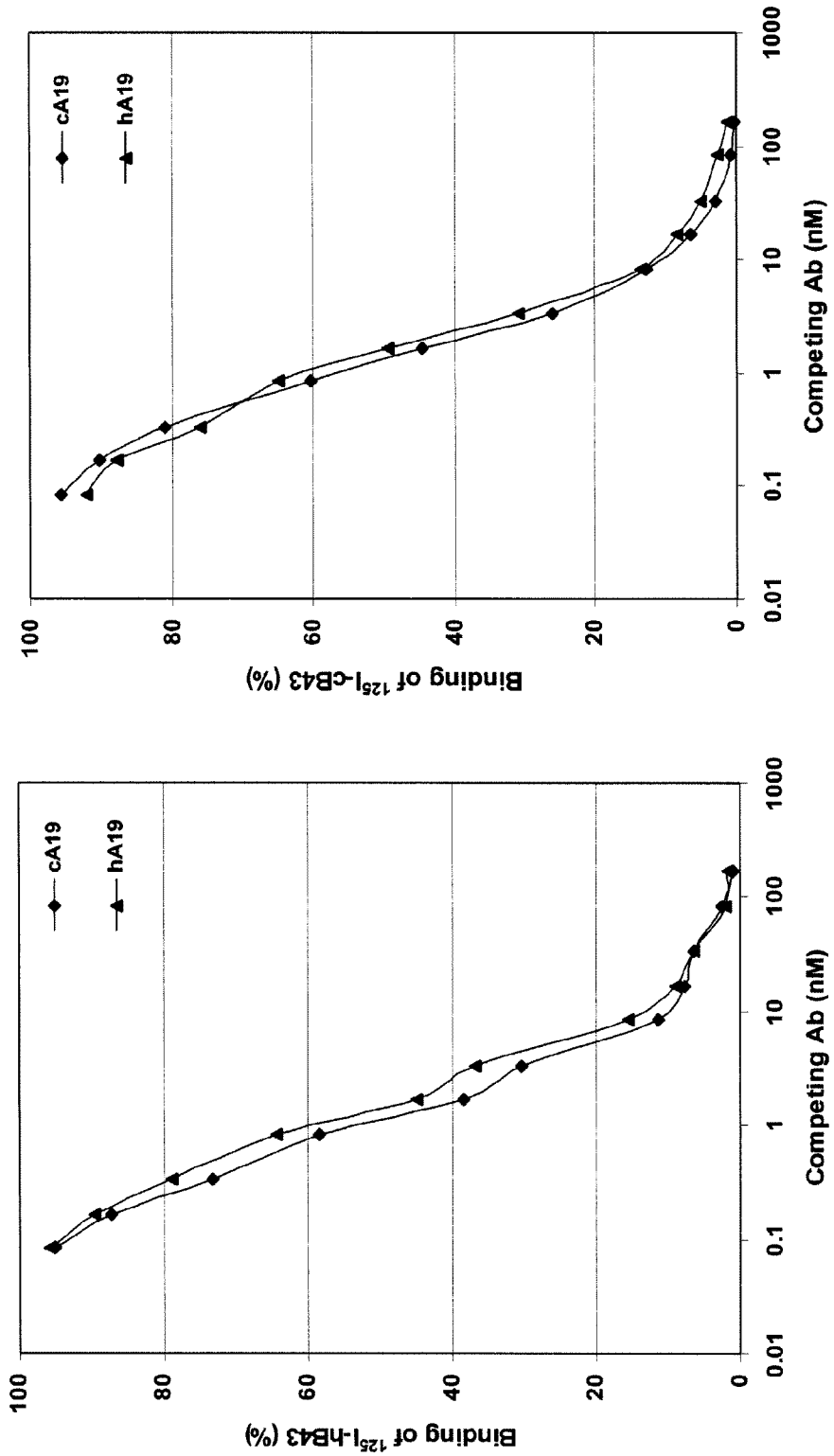
FIG. 5 shows the results of cell surface competitive binding assay to compare the binding specificity and activity of the humanized A19 antibody, hA19, with that of cA19.
Figure 6:
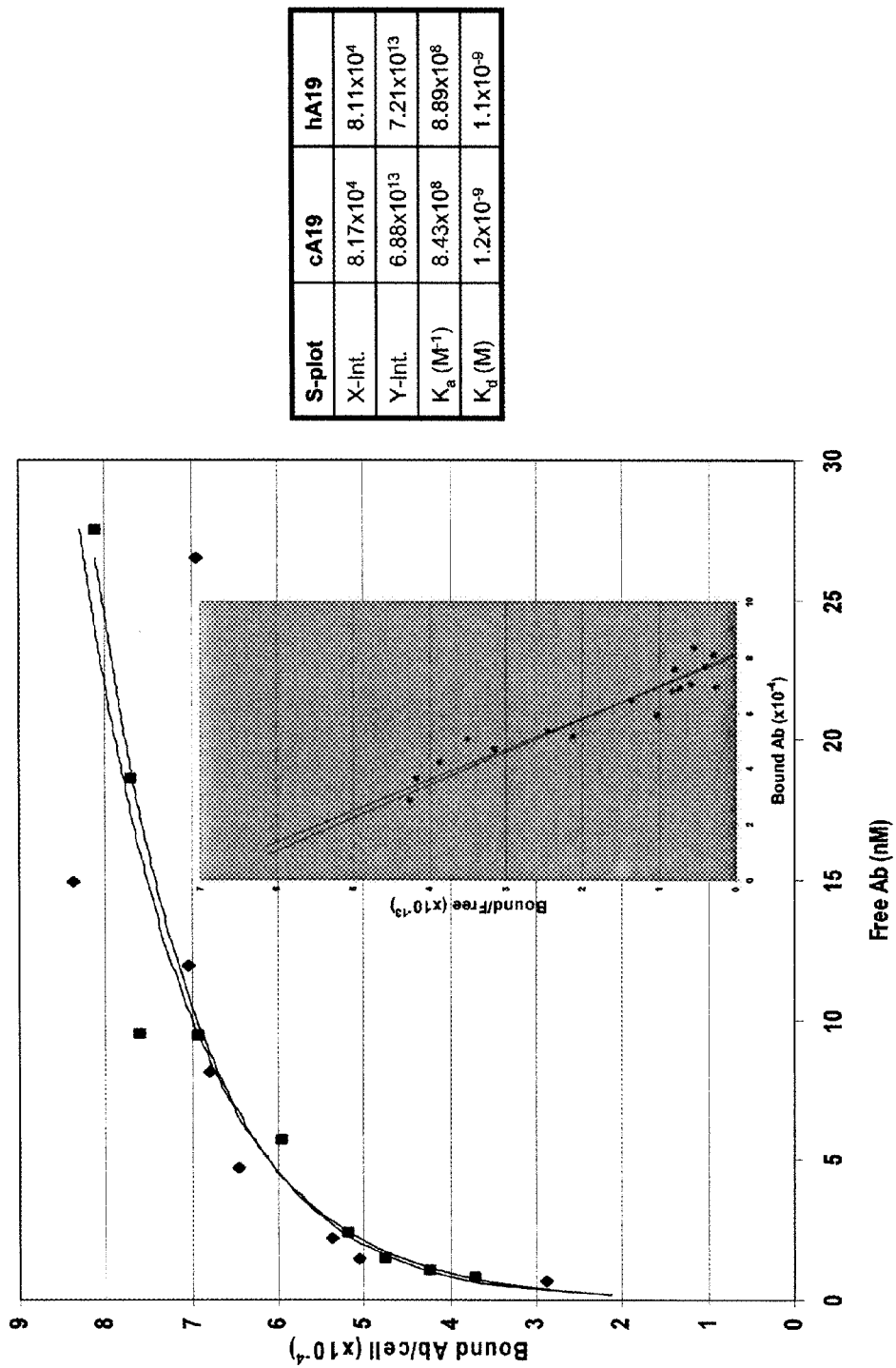
FIG. 6 shows the determination of the Ag-binding affinity (avidity) of the anit-CD19 Ab by the direct cell surface binding and Scatchard plot analysis. Varying concentrations of $^{125}$I hA19 (diamonds) or $^{112}$In-cA19 (squares) were incubated with Raji cells at 40° C. for 1 h. Total and bound radioactivities were counted and analyzed by Scatchard plot as shown in the inset. hA19 showed virtually same binding affinity as cA19. As shown the apparent dissociation constant values were calculated to be 1.1 and 1.2 nM for hA19 and cA19, respectively.

The antigen-binding affinity (avidity) constant of hA19 was determined by direct cell surface binding assay of the radiolabeled Ab and Scatchard plot analysis, in comparison to that of cA19. Briefly, hA19 and cA19 were labeled with $^{125}$I by the chloramines-T method. Varying amounts of either $^{125}$I-hA19 or $^{125}$I-cA19 were incubated with $2\times10^5$ Raji cells at 4° C. for 2 h and unbound antibodies were removed by washing. The cell-associated radioactivity was counted and Scatchard plot analysis was performed to determine the maximum number of hA19 and cA19 binding sites per cell and the apparent dissociation constants of the equilibrium binding. As shown in FIG. 5, hA19 showed virtually the same binding affinity as cA19. The apparent dissociation constant values for these two antibodies were calculated to be 1.1 and 1.2 nM, respectively.

Example 5

Sequence Variants of hA19

The humanized anti-CD19 MAb (hA19) described in Example 2 above was expressed in Sp2/0 cells, but the productivity of resulting clones was low. Numerous transfections (a total of 15) were performed and hundreds of clones were screened. The productivities of positive clones remained between 0.5-3 µg/ml and amplification with methotrexate did not improve the productivities of subjected clones.

Modifying the Vk Gene Sequence to Reduce the AT Contents

To generate a higher producing hA19 clone, two approaches were used. The first approach (hA19VkpdHL2) was to re-design the hA19Vk gene sequence to reduce the AT content, which presumably has a negative impact on the Ab gene expression. The new hA19Vk gene was synthesized, assembled, and used to reconstruct the expression vector for hA19.

After construction of hA19VkpdHL2 was completed and DNA sequencing confirmed the sequences to be correct, a maxiprep was performed to prepare the plasmids for transfection. Three transfections were performed: #739 (hA19VkpdHL2#1), #740 (hA19VkpdHL2#5) and #741 (hB43pdHL2#1). SP-E26 cells and 10 µg of SalI-linearized DNA were used. MTX selection (0.075 µM) started 48 h post electroporation. An ELISA was used to screen transfections for positive clones. Transfection #739 yielded 31 positive clones (13 were selected), #740 yielded 49 positive clones (13 were selected), and #741 yielded 41 positive clones (19 were selected). The productivities were determined and monitored by ELISA and ranged from 0.5-3 µg/ml, the same as observed for the original hA19 construct.

Two serum-free transfections were performed: #746 (hA19VkpdHL2#1) and #747 (hB43pdHL2#1). SP-ESF cells and 10 µg of SalI-linearized DNA were used for both transfections. MTX selection (0.075 µM) started 48 h post electroporation. Transfection #746 yielded 9 positive clones and #747 yielded 6 positives. The positives were expanded to a 48 well plate and amplified to 0.2 µM MTX. The 45 clones from transfections #739, #740, and #741 were narrowed down to 12 (based on an ELISA reading above 1.0 µg/ml) and the MTX was increased to 0.15 µM. The initial $p_{max}$ of the serum-free clones was determined and the productivities were similar to the clones in serum medium (0.5-1.5 µg/ml).

Two more serum transfections were performed: #756 (hA19VkpdHL2#5) and #757 (hB43pdHL2#1). The transfection conditions were the same as before, however, the slow growing clones were given time to develop to see if the $p_{max}$ would be higher. Transfection #756 yielded 19 positive clones and #757 yielded 8 positive clones. The $p_{max}$ of transfections #756 and #757 were compared with transfections #739, #740, #741, #746, and #747. The productivities were similar (~0.5-3 µg/ml). The best producers were selected (739.1A9, 740.1B1, and 756.2G7) and amplified to 0.2 µM MTX. Results reported in Table 2 show an average antibody productivity of between 2 and 3 µg/ml.

TABLE 1

Comparison of initial positives and $p_{max}$ values in both 10% FBS and serum-free conditions.

|  | Initial Positives | $p_{max}$ (ug/ml) |
|---|---|---|
| SP-E26 |  |  |
| #739 | 31 | 0.5-3 |
| #740 | 49 | 0.5-3 |
| #741 | 41 | 0.5-3 |
| #756 | 19 | 0.5-3 |
| #757 | 8 | 0.5-3 |
| SP-ESF |  |  |
| #746 | 9 | 0.5-1.5 |
| #747 | 6 | 0.5-1.5 |

TABLE 2

Average $p_{max}$ and standard deviation values from the three best hA19VkpdHL2 clones.

| 0.2 µM MTX | Avg. (ug/ml) | St. Dev. |
|---|---|---|
| 739.1A9 | 2.96 | ±1.40 |
| 740.1B1 | 2.30 | ±0.30 |
| 756.2G7 | 2.95 | ±0.70 |

Cell-Based Antibody Dependent Cytotoxicity Assay

To determine whether or not the redesigned vector produced active antibody, two liters of clone 756.2G7 were purified by protein-A purification. The purification yielded 7.3 mgs of anti-CD-19 Ab. HPLC and SDS-PAGE showed the purified protein to be pure (not shown). The purified protein was used to examine the effects of antibody treatment on cell proliferation and death. A cell based antibody dependent cytotoxicity assay was performed to compare hA19, hA20, and hLL2 with and without GAH IgG and Fc fragment. Daudi D1-1 and SP-E26 cells were plated in two 48 well plates at a final density of 150,000 cells/ml. hA19, hA20 and hLL2 were diluted (final concentration of 10 µg/ml) in complete medium (RPMI for D1-1 and SFM for SP-E26) both with and without GAH (final concentration of 40 µg/ml). The Ab mixtures were added to the plate and placed on a shaker for a few minutes and then put in the incubator. An MIT was performed at day5 3 and 4. The results from day 3 showed that there was no difference in cell growth in SP-E26 cells. The D1-1 cells show inhibition of cell growth in hA19+GAH and hA20+GAH. These results showed that the redesigned hA19 is active.

hA19FpdHL2

The second approach (hA19FpdHL2) was to re-design the hA19VH gene to replace the heavy chain (VH) framework region amino acid residue serine 91 with the consensus phenylalanine residue. The TCT codon for S91 in hA19VHpdHL2 was changed to a UC codon for F91 in hA19FVHpdHL2. The new hA19F gene was synthesized, assembled, and used to re-construct the expression vector for hA19.

After construction of hA19FpdHL2 was completed and DNA sequencing confirmed the sequences to be correct a maxiprep was performed to prepare the plasmids for transfection. Two transfections were performed: #762

(hA19FpdHL2#2) and #763 (hA19FpdHL2#3). Transfection conditions were the same as transfections #739, #740, and #741. An ELISA was used to screen both transfections for positive clones. Transfection #762 yielded 13 positive clones (8 were selected), and #743 yielded 18 positive clones (16 were selected). The initial productivities were determined by ELISA, shown in Table 3.

TABLE 3

Average $p_{max}$ and standard deviation values from the hA19FpdHL2 clones that were selected.

| 0.075 μM MTX | Avg. (ug/ml) | St. Dev. |
|---|---|---|
| 762.2D6 | 42.42 | |
| 762.2H9 | 11.34 | |
| 762.2B10 | 14.86 | |
| 762.2D4 | 12.69 | |
| 762.2A10 | 15.96 | |
| 762.2C11 | 6.34 | |
| 762.2F11 | 9.17 | |
| 763.2B2 | 11.57 | 3.39 |
| 763.2G2 | 11.18 | 1.74 |
| 763.2B4 | 9.08 | 5.27 |
| 763.2D4 | 10.88 | 13.64 |
| 763.2E11 | 15.33 | 4.32 |
| 763.2C4 | 11.57 | 8.13 |
| 763.2B5 | 2.94 | 1.13 |
| 763.2H5 | 7.46 | 5.39 |
| 763.2C5 | 18.91 | 10.70 |
| 763.2H6 | 6.54 | 4.09 |
| 763.2A6 | 14.17 | 12.64 |
| 763.2A9 | 2.35 | |
| 763.2A10 | 2.95 | 0.95 |
| 763.2B12 | 15.76 | 6.95 |
| 763.2C12 | 6.28 | 5.50 |
| 763.2D3 | 6.65 | |

Transfection of host cells with the new vector resulted in more than 100 positive clones. We randomly picked 30 clones for evaluation. Most of these clones were estimated to have yields of antibody production in cell culture of between 5-25 mg/L of IgG. This contrasts with the cell culture productivity of the clones generated previously, which were in the range of 1-2 mg/L. Therefore, we conclude that the substitution Ser91Phe resulted in a significant increase in the expression level of the hA19 antibody, with about a 10-fold increase in antibody production. This surprising and unexpected result allows substantially greater amounts of the antibody protein to be produced in cell culture using expression in mammalian cell lines.

Example 6

Therapy of Non-Hodgkin's Lymphoma

A patient with indolent, follicular-cell NHL relapses after chemotherapy including dexamethasone, and has disease in the chest (para-aortic lymph nodes), an enlarged and involved spleen, and enlarged cervical lymph nodes. The patient is given a course of 300 mg/m$^2$ each of hA19 MAb combined with humanized anti-CD20 MAb (hA20) sequentially on the same day by i.v. infusion, weekly for 4 weeks, each time being premedicated with TYLENOL® and BENADRYL® according to standard, published doses for suppressing infusion-related reactions. Four weeks later, the patient returns for the first follow-up examination and the only observation is that some of the palpable lymph nodes feel softer. Upon returning 3 months following the first therapy cycle, the patient's chest disease appears to have become reduced by 40% on CT scan, the spleen is about half the pre-therapy size, and the cervical lymph nodes are almost gone. The patient is then given a retreatment cycle, and another three months later appears to have a normal-sized spleen, no cervical lymph nodes palpable or measurable on CT scan, and only a small, 1.5-cm lesion in the chest. The patient continues to appear almost free of disease for another 4 months.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All of the publications and patent applications and patents cited in this specification are herein incorporated in their entirety by reference.

What is claimed is:

1. A method of treating a B cell lymphoma comprising administering a humanized antibody or antigen-binding fragment thereof that binds CD19 to a subject with a B cell lymphoma, wherein the B cells associated with the B cell lymphoma express CD19 antigen, wherein the humanized anti-CD19 antibody comprises the light chain complementarity determining region (CDR) sequences CDR1 KASQS-VDYDGDSYLN (SEQ ID NO: 16); CDR2 DASNLVS (SEQ ID NO: 17); and CDR3 QQSTEDPWT (SEQ ID NO: 18) and the heavy chain CDR sequences CDR1 SYWMN (SEQ ID NO: 19); CDR2 QIWPGDGDTNYNGKFKG (SEQ ID NO: 20) and CDR3 RETTTVGRYYYAMDY (SEQ ID NO: 21), wherein said humanized anti-CD19 antibody or fragment thereof comprises human antibody framework (FR) and constant region sequences with one or more framework region amino acid residues substituted from the corresponding framework region sequences of the parent murine antibody, and wherein said substituted FR residues comprise the substitution of phenylalanine for serine at Kabat residue 91 of the heavy chain variable region.

2. The method of claim 1, wherein the humanized anti-CD19 antibody or fragment thereof is a naked antibody or fragment.

3. The method of claim 2, further comprising administering to said subject concurrently or sequentially at least one humanized, chimeric, human or murine MAb reactive with an antigen selected from the group consisting of CD5, CD14, CD15, CD19, CD20, CD21, CD22, CD23, CD25, CD37, CD38, CD40, CD40L, CD46, CD52, CD54, CD66(a-d), CD74, CD80, CD126, CD138, MUC1, Ia, HM1.24, HLA-DR, tenascin, VEGFR, P1GF, ED-B fibronectin, HLA-DR invariant chain, T101, TAC, TRAIL-R1 (DR4) and TRAIL-R2 (DR5).

4. The method of claim 1, wherein the humanized anti-CD19 antibody or fragment thereof is conjugated to a drug selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, thalidomide, endostatin, taxols, camptothecins, anthracyclines and taxanes.

5. The method of claim 1, wherein the humanized anti-CD19 antibody or fragment thereof is conjugated to a toxin selected from the group consisting of ricin, abrin, alpha toxin, saporin, onconase, ribonuclease (RNase), DNase I, Staphylococcal enterotoxin-A, pokeweed antiviral protein, gelonin, diphtheria toxin, Pseudomonas exotoxin and Pseudomonas endotoxin.

6. The method of claim 1, wherein the humanized anti-CD19 antibody or fragment thereof is conjugated to an anti-angiogenic agent selected from the group consisting of angiostatin, endostatin, vasculostatin, canstatin, maspin, an anti-VEGFR (vascular endothelium growth factor receptor) antibody, an anti-P1GF (placental growth factor) antibody and an anti-ED-B fibronectin antibody.

7. The method of claim 1, wherein the humanized anti-CD19 antibody or fragment thereof is conjugated to an immunomodulator selected from the group consisting of a cytokine, a stem cell growth factor, a lymphotoxin, a hematopoietic factor, a colony stimulating factor (CSF), an interferon (IFN), erythropoietin and thrombopoietin.

8. The method of claim 7, wherein the lymphotoxin is tumor necrosis factor-$\alpha$(TNF-$\alpha$) or TNF-$\beta$, said hematopoietic factor is interleukin-1 (IL-1), IL-2, IL-3, IL-6, IL-10, IL-12, IL-18 or IL-21, said colony stimulating factor is granulocyte-colony stimulating factor (G-CSF) or granulocyte macrophage-colony stimulating factor (GM-CSF), said interferon is interferon-alpha, -beta or -gamma, and said stem cell growth factor is S1 factor.

9. The method of claim 1, wherein the humanized anti-CD19 antibody or fragment thereof is conjugated to a radionuclide selected from the group consisting of $^{225}$Ac, $^{67}$Ga, $^{90}$Y, $^{111}$In, $^{131}$I, $^{125}$I, $^{186}$Re, $^{188}$Re, $^{177}$Lu, $^{32}$P, $^{64}$Cu, $^{67}$Cu, $^{212}$Bi, $^{213}$Bi and $^{211}$At.

10. The method of claim 1, wherein the humanized anti-CD19 MAb or fragment thereof is administered as part of a bispecific or multispecific antibody that contains at least one other antibody or fragment thereof that binds to an antigen selected from the group consisting of CD5, CD14, CD15, CD19, CD20, CD21, CD22, CD23, CD25, CD37, CD38, CD40, CD40L, CD46, CD52, CD54, CD66(a-d), CD74, CD80, CD126, CD138, MUC, Ia, HM 1.24, HLA-DR, tenascin, VEGFR, P1GF, ED-B fibronectin, HLA-DR invariant chain, T101, TAC, TRAIL-R1 (DR4) and TRAIL-R2 (DR5).

11. The method of claim 1, wherein the substitution of phenylalanine for serine at VH residue 91 results in an increase in expression level of the anti-CD 19 antibody in cell culture.

12. A method of treating a B cell leukemia comprising administering a humanized antibody or antigen-binding fragment thereof that binds CD19 to a subject with a B cell leukemia, wherein the B cells associated with the B cell leukemia express CD19 antigen, wherein the humanized anti-CD19 antibody comprises the light chain complementarity determining region (CDR) sequences CDR1 KASQS-VDYDGDSYLN (SEQ ID NO: 16); CDR2 DASNLVS (SEQ ID NO: 17); and CDR3 QQSTEDPWT (SEQ ID NO: 18) and the heavy chain CDR sequences CDR1 SYWMN (SEQ ID NO: 19); CDR2 QIWPGDGDTNYNGKFKG (SEQ ID NO:

20) and CDR3 RETTTVGRYYYAMDY (SEQ ID NO: 21), wherein said humanized anti-CD 19 antibody or fragment thereof comprises human antibody framework (FR) and constant region sequences with one or more framework region amino acid residues substituted from the corresponding framework region sequences of the parent murine antibody, and wherein said substituted FR residues comprise the substitution of phenylalanine for serine at Kabat residue 91 of the heavy chain variable region.

13. The method of claim 12, wherein the humanized anti-CD19 antibody or fragment thereof is a naked antibody or fragment.

14. The method of claim 12, wherein the humanized anti-CD19 antibody or fragment thereof is conjugated to a drug selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, thalidomide, endostatin, taxols, camptothecins, anthracyclines and taxanes.

15. The method of claim 12, wherein the humanized anti-CD 19 antibody or fragment thereof is conjugated to a toxin selected from the group consisting of ricin, abrin, alpha toxin, saporin, onconase, ribonuclease (RNase), DNase I, Staphylococcal enterotoxin-A, pokeweed antiviral protein, gelonin, diphtheria toxin, Pseudomonas exotoxin and Pseudomonas endotoxin.

16. The method of claim 12, wherein the humanized anti-CD19 antibody or fragment thereof is conjugated to an anti-angiogenic agent selected from the group consisting of angiostatin, endostatin, vasculostatin, canstatin, maspin, an anti-VEGFR (vascular endothelium growth factor receptor) antibody, an anti-P1GF (placental growth factor) antibody and an anti-ED-B fibronectin antibody.

17. The method of claim 12, wherein the humanized anti-CD19 antibody or fragment thereof is conjugated to an immunomodulator selected from the group consisting of a cytokine, a stem cell growth factor, a lymphotoxin, a hematopoietic factor, a colony stimulating factor (CSF), an interferon (IFN), erythropoietin and thrombopoietin.

18. The method of claim 17, wherein the lymphotoxin is tumor necrosis factor-a (TNF-β) or TNF-β, said hematopoietic factor is interleukin-1 (IL-1), IL-2, IL-3, IL-6, IL-10, IL-12, IL-18 or IL-21, said colony stimulating factor is granulocyte-colony stimulating factor (G-CSF) or granulocyte macrophage-colony stimulating factor (GM-CSF), said interferon is interferon-alpha, -beta or -gamma, and said stem cell growth factor is S1 factor.

19. The method of claim 12, wherein the humanized anti-CD19 antibody or fragment thereof is conjugated to a radionuclide selected from the group consisting of $^{225}AC$, $^{67}Ga$, $^{90}Y$, $^{111}In$, $^{131}I$, $^{125}I$, $^{186}Re$, $^{188}Re$, $^{177}Lu$, $^{32}P$, $^{64}Cu$, $^{67}Cu$, $^{212}Bi$, $^{213}Bi$ and $^{211}At$.

20. The method of claim 12, wherein the humanized anti-CD19 MAb or fragment thereof is administered as part of a bispecific or multispecific antibody that contains at least one other antibody or fragment thereof that binds to an antigen selected from the group consisting of CD5, CD14, CD15, CD19, CD20, CD21, CD22, CD23, CD25, CD37, CD38, CD40, CD40L, CD46, CD52, CD54, CD66(a-d), CD74, CD80, CD126, CD138, MUC, Ia, HM1.24, HLA-DR, tenascin, VEGFR, P1GF, ED-B fibronectin, HLA-DR invariant chain, T101, TAC, TRAIL-R1 (DR4) and TRAIL-R2 (DR5).

* * * * *